(12) United States Patent
Butlin et al.

(10) Patent No.: US 6,878,712 B1
(45) Date of Patent: Apr. 12, 2005

(54) AMIDES AS INHIBITORS FOR PYRUVATE DEHYDROGENASE

(75) Inventors: Roger John Butlin, Macclesfield (GB); Janet Elizabeth Pease, Macclesfield (GB); Michael Howard Block, Macclesfield (GB); Thorsten Nowak, Macclesfield (GB); Jeremy Nicholas Burrows, Macclesfield (GB); David Stephen Clarke, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 7 days.

(21) Appl. No.: 10/069,995

(22) PCT Filed: Aug. 30, 2000

(86) PCT No.: PCT/GB00/03297

§ 371 (c)(1),
(2), (4) Date: Jun. 17, 2002

(87) PCT Pub. No.: WO01/17942

PCT Pub. Date: Mar. 15, 2001

(30) Foreign Application Priority Data

Sep. 4, 1999 (GB) .............................................. 9920821
Dec. 18, 1999 (GB) .............................................. 9929835

(51) Int. Cl.$^7$ .................... A61K 31/495; A61K 31/496; C07D 295/16; C07D 295/26; C07D 409/12
(52) U.S. Cl. ........................... 514/252.13; 514/255.01; 514/327; 514/329; 514/330; 514/415; 544/383; 544/379; 544/388; 546/221; 546/223; 546/224; 546/226; 548/491
(58) Field of Search ................................ 544/383, 379, 544/388; 514/252.13, 255.01

(56) References Cited

U.S. PATENT DOCUMENTS

| 4,537,618 A | 8/1985 | Schurter et al. |
| 5,248,693 A | 9/1993 | Gerspacher et al. |
| 5,486,515 A | 1/1996 | Brown et al. |
| 5,510,386 A | 4/1996 | Empfield et al. |
| 6,369,273 B1 | 4/2002 | Butlin |
| 6,498,275 B1 | 12/2002 | Butlin et al. |

FOREIGN PATENT DOCUMENTS

| CA | 1 228 355 | 10/1987 |
| EP | 0 002 309 | 6/1979 |
| EP | 0 002 892 | 7/1979 |
| EP | 0 040 932 | 12/1981 |
| EP | 0 079 191 | 5/1983 |
| EP | 0 096 002 | 12/1983 |
| EP | 0 100 172 | 2/1984 |
| EP | 0 253 500 | 1/1988 |
| EP | 0 253 503 | 1/1988 |
| EP | 0 524 781 | 1/1993 |
| EP | 0 617 010 | 9/1994 |
| EP | 0 625 511 | 11/1994 |
| EP | 0 625 516 | 11/1994 |
| GB | 2 278 054 | 11/1994 |
| WO | 93/10094 | 5/1993 |
| WO | 93/23358 | 5/1993 |
| WO | 94/26739 | 11/1994 |
| WO | 96/28151 | 9/1996 |
| WO | 97/38124 | 10/1997 |
| WO | 99/44618 | 9/1999 |
| WO | 99/47508 | 9/1999 |
| WO | 99/62506 | 12/1999 |
| WO | 99/62873 | 12/1999 |
| WO | 01/17942 | 3/2001 |
| WO | 01/17955 | 3/2001 |
| WO | 01/17956 | 3/2001 |

OTHER PUBLICATIONS

Timmons et al. J. Clin. Invest., vol. 97, p. 879–883 (1996).*
Aicher et al., "(R)–3,3,3–trifluoro–2–hydroxy–2–methylpropionamides are orally active inhibitors of pyruvate dehydrogenase kinase", Journal of Medicinal Chemistry, American Chemical Society, vol. 42, No. 15, Jul. 1999, pp. 2741–2746, XP002122777.
Mann et al, Diverse mechanisms of inhibition of pyruvate dehydrogenase inhibitors, Biochim, Biophys. ACTA, 2000, 1480(1–2) XP000979112.
Aicher et al., "Secondary amides of (R)–3,3,3–Trifluoro–2–hydroxo–2–methylpropaionicacid as inhibitors of pyruvate dehydrogenase kinase", J. Med. Chem., vol. 43, No, 2, Jan. 2000, pp. 236–249, XP002158429.

(Continued)

*Primary Examiner*—Emily Bernhardt
(74) *Attorney, Agent, or Firm*—Morgan, Lewis & Bockius LLP

(57) ABSTRACT

A compound of formula (I):

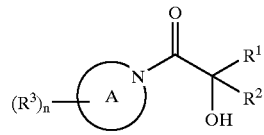

(I)

wherein:
  Ring A is a nitrogen linked mono or bicyclic heterocyclic ring as defined within;
  $R^1$ and $R^2$ are independently $C_{1-3}$alkyl optionally substituted by fluoro or chloro;
  or $R^1$ and $R^2$ together with the carbon atom to which they are attached, form a $C_{3-5}$cycloalkyl ring optionally substituted by fluoro;
  $R^3$ is defined within; and
  n is 0–5; wherein the values of $R^3$ may be the same or different;
or a pharmaceutically acceptable salt or an in vivo hydrolysable ester thereof is described. The use of compounds of formula (I) in the production of an elevation of PDH activity in a warm-blooded animal such as a human being are also described. Pharmaceutical compositions, methods and processes for preparation of compounds of formula (I) are detailed.

13 Claims, No Drawings

OTHER PUBLICATIONS

Bayles et al., "A Smiles Rearrangement Involving Non–Activated Aromatic Systems; the Facile Conversion of Phenols to Anilines", Synthesis, 1977, vol. 1. pp. 33–34.

Bayles et al.,, "The Smiles Rearrangement of 2–Aryloxy–2–methylpropanamides. Synthesis of N–Aryl–2–hydroxy–2–methyl–propanamides", Synthesis, 1977, vol. 1, pp. 31–33.

Bebernitz et al., "Anilides of (R)–Trifluoro–2–hydroxy–2–methylpropionic Acid as Inhibitors of Pyruvate Dehydrogenase Kinase", J. Med. Chem., 2000, vol. 43, No. 11, pp. 2257–2266.

Empfield et al., "4–sulfonamidoanilide Tertiary Carbinols: A Novel Series Of Potassium Channel Openers", Bioorg Med. Chem. Letters, 1997, vol. 7, No. 7, pp. 775–778, XP004136128s e table I, compounds e, f.

Fenwick, "The Synthesis of 2,2–Bis(Trifluoromethyl)Benzopyran Derivatives: A New Route to an Import Class of Postassium Channel Activators", Tetrahedron Letters, vol. 34, No. 11, 1993, pp. 1993.

Furr et al., "A Novel Non–Steroidal, Peripherally Selective Antiandrogen", J. Endrocrinol., 1987, vol. 113 (3), R7–R9.

Glen et al., Structure–Activity Relationships among Nonsteriodal Antiandrogens, Third SCI–RSC Medicinal Chemistry Symposium, 1986, vol. 55, pp. 345–361.

Grant et al., "Anilide Tertiary Carbinols: A New Structural Class Of Potent Potassium Channel Openers", Bioorg. Med. Chem. Lett., 1993, vol. 3 (12), pp. 2723–2724.

Howe et al., "Zeneca ZD6169: A Novel $K_{ATP}$ Channel Opener with in Vivo Selectivity for Urinary Bladder", J. Pharmacol. Exp. Ther. 1995, vol. 274 (2), pp, 884–890.

Jackman et al., "Studies in the Field of Diuretics", J. Pharm. and Pharmacol., vol. 12, 1960, pp. 648–655; Chemical Abstracts, vol. 55, No. 9, May 1, 1961, Columbus, Ohio, US; abstract No. 8336a, XP002107578 see abstract, col. 8336, lines 8–9 &.

Li et al., "Zeneca ZD6169 and Its Analogs from a Novel Series of Anilide Tertiary Carbinols: in vitro $K_{ATP}$ Channel Opening Activity in Bladder Detrusor", Pharmacology, 1995, vol. 51, pp. 33–42.

Morris et al., "Hydrogen Bonding Parameters In The S.A.R. of Non–Steroidal Anti–Androgens", Pharmacol. Libr., 1987, vol. 10, pp. 204–206.

Morris et al., "Non–Steroidal Antiandrogens. Design of Novel Compounds Based on an Infrared Study of the Dominant Conformationand Hydrogen–Bonding Properties of a Series of Anilide Antiandrogens", J. Med. Chem. 1991, vol. 34, pp, 447–455.

Ohnmacht et al., N–Aryl–3,3, 3–trifluoro–2–hydroxy–2–methylpropanamides: $K_{ATP}$ Potassium Channel Openers. Modifications on the Western Region, J. Med. Chem., 1996, vol. 39 (23), pp. 4592–4601.

Russell, "Crystal Receptor Models In Medicinal Chemistry: Application To The Generation of Highly Potent Potassium Channel Openers", Bioorg. Med. Chem. Lett. 1996, vol. 6 (7), pp. 913–918.

Tenthorey et al.; "New Antiarrhythmic Agents. 3. Primary β–Amino Anilides", J. Med. Chem. 1979, vol. 22 (10), pp. 1182–1186.

Trivedi et al., "K–Channel Opening Activity of ZD6169 and Its Analogs: Effect on $^{86}$Rb Efflux and $^{3}$H–1075 Binding in Bladder Smooth Muscle", Pharmacology, 1995, vol. 50 (6), pp. 388–397.

Tucker et al., "Nonsteroidal Antiandrogens. Synthesis and Structure–Activity Relationships of 3–Substituted Derivatives of 2–Hydroxypropionanilides", J. Med. Chem., 1988, vol. 31, pp. 954–959.

Tucker et al., "Resolution of the Nonsteriodal Antiandrogen 4'–Cyano–3–[(4–fluorophenyl)sulfonyl]–2–hydroxy–2–methyl–3'–(trifluoromethyl)– propionanilide and the Determination of the Absolute Configuration of the Active Enantiomer", J. Med. Chem. 1988. vol. 31 (4), pp. 885–887.

Wakeling et al., "Receptor Binding And Biological Activity Of Steriodal and Nonsteriodal Antiandrogens", J. Steriod Biochem., 1981, vol. 15, pp. 355–359.

* cited by examiner

AMIDES AS INHIBITORS FOR PYRUVATE DEHYDROGENASE

The present invention relates to compounds which elevate pyruvate dehydrogenase (PDH) activity, processes for their preparation, pharmaceutical compositions containing them as active ingredient, methods for the treatment of disease states associated with reduced PDH activity, to their use as medicaments and to their use in the manufacture of medicaments for use in the elevation of PDH activity in warm-blooded animals such as humans, in particular the treatment of diabetes mellitus, peripheral vascular disease and myocardial ischaemia in warm-blooded animals such as humans, more particularly to their use in the manufacture of medicaments for use in the treatment of diabetes mellitus in warm-blooded animals such as humans.

Within tissues adenosine triphosphate (ATP) provides the energy for synthesis of complex molecules and, in muscle, for contraction. ATP is generated from the breakdown of energy-rich substrates such as glucose or long chain free fatty acids. In oxidative tissues such as muscle the majority of the ATP is generated from acetyl CoA which enters the citric acid cycle, thus the supply of acetyl CoA is a critical determinant of ATP production in oxidative tissues. Acetyl CoA is produced either by β-oxidation of fatty acids or as a result of glucose metabolism by the glycolytic pathway. The key regulatory enzyme in controlling the rate of acetyl CoA formation from glucose is PDH which catalyses the oxidation of pyruvate to acetyl CoA and carbon dioxide with concomitant reduction of nicotinamide adenine dinucleotide (NAD) to NADH.

In disease states such as biotin non-insulin dependent (NIDDM) and insulin-dependent diabetes mellitus (IDDM), oxidation of lipids is increased with a concomitant reduction in utilisation of glucose, which contributes to the hyperglycaemia. Reduced glucose utilisation in both IDDM and NIDDM is associated with a reduction in PDH activity. In addition, a further consequence of reduced PDH activity may be that an increase in pyruvate concentration results in increased availability of lactate as a substrate for hepatic gluconeogenesis. It is reasonable to expect that increasing the activity of PDH could increase the rate of glucose oxidation and hence overall glucose utilisation, in addition to reducing hepatic glucose output. Another factor contributing to diabetes mellitus is impaired insulin secretion, which has been shown to be associated with reduced PDH activity in pancreatic β-cells (in a rodent genetic model of diabetes millitus Zhou et al. (1996) Diabetes 45: 580–586).

Oxidation of glucose is capable of yielding more molecules of ATP per mole of oxygen than is oxidation of fatty acids. In conditions where energy demand may exceed energy supply, such as myocardial ischaemia, intermittent claudication, cerebral ischemia and reperfusion, (Zaidan et al., 1998; J. Neurochem. 70: 233–241), shifting the balance of substrate utilisation in favour of glucose metabolism by elevating PDH activity may be expected to improve the ability to maintain ATP levels and hence function.

An agent which is capable of elevating PDH activity may also be expected to be of benefit in treating conditions where an excess of circulating lactic acid is manifest such as in certain cases of sepsis.

The agent dichloroacetic acid (DCA) which increases the activity of PDH after acute administration in animals, (Vary et al., 1988; Circ. Shock, 24: 3–18), has been shown to have the predicted effects in reducing glycaemia, (Stacpoole et al., 1978; N. Engl. J. Med. 298: 526–530), and as a therapy for myocardial ischaemia (Bersin and Stacpoole 1997; American Heart Journal, 134: 841–855) and lactic acidaemia, (Stacpoole et al., 1983; N. Engl. J. Med. 309: 390–396).

PDH is an intramitochondrial multienzyme complex consisting of multiple copies of several subunits including three enzyme activities E1, E2 and E3, required for the completion of the conversion of pyruvate to acetyl CoA (Patel and Roche 1990; FASEB J., 4: 3224–3233). E1 catalyses the non-reversible removal of $CO_2$ from pyruvate; E2 forms acetyl CoA and E3 reduces NAD to NADH. Two additional enzyme activities are associated with the complex: a specific kinase which is capable of phosphorylating E1 at three serine residues and a loosely-associated specific phosphatase which reverses the phosphorylation. Phosphorylation of a single one of the three serine residues renders the E1 inactive. The proportion of the PDH in its active (dephosphorylated) state is determined by a balance between the activity of the kinase and phosphatase. The activity of the kinase may be regulated in vivo by the relative concentrations of metabolic substrates such as NAD/NADH, CoA/acetylCoA and adenine diphosphate (ADP)/ATP as well as by the availability of pyruvate itself.

European Patent Publication Nos. 617010 and 524781 describes compounds which are capable of relaxing bladder smooth muscle and which may be used in the treatment of urge incontinence. We have found that the compounds of the present invention are very good at elevating PDH activity, a property nowhere disclosed in EP 0617010 and EP 524781.

The present invention is based on the surprising discovery that certain compounds elevate PDH activity, a property of value in the treatment of disease states associated with disorders of glucose utilisation such as diabetes mellitus, obesity, (Curto et al., 1997; Int. J. Obes. 21: 1137–1142), and lactic acidaemia. Additionally the compounds may be expected to have utility in diseases where supply of energy-rich substrates to tissues is limiting such as peripheral vascular disease, (including intermittent claudication), cardiac failure and certain cardiac myopathies, muscle weakness, hyperlipidaemias and atherosclerosis (Stacpoole et al., 1978; N. Engl. J. Med. 298: 526–530). A compound that activates PDH may also be useful in treating Alzheimer's disease (AD) (J Neural Transm (1998) 105, 855–870).

Accordingly, the present invention provides a compound of formula (I):

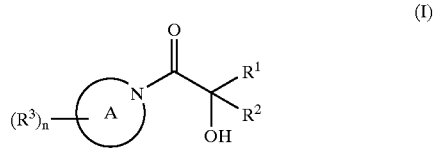

wherein:
Ring A is a nitrogen linked mono or bicyclic heterocyclic ring; wherein if said heterocyclic group contains an —NH— moiety that nitrogen is optionally substituted by $R^4$—D—;

$R^1$ and $R^2$ are independently $C_k$alkyl optionally substituted by 1 to 2k+1 atoms selected from fluoro and chloro wherein k is 1–3;

or $R^1$ and $R^2$ together with the carbon atom to which they are attached, form a $C_m$cycloalkyl ring optionally substituted by 1 to 2m−2 fluorine atoms wherein m is 3–5;

$R^3$ is a substituent on carbon and is halo, hydroxy, cyano, formyl, amino, nitro, carboxy, carbamoyl, ureido, thiol, sulphamoyl or $R^5$—E—;

$R^4$ is $C_{1-6}$alkyl, phenyl or a heterocyclic group, wherein in $R^4$ any $C_{1-6}$alkyl, phenyl or heteorcyclic groups (on a ring carbon) may be optionally substituted by one or more $R^6$ and if said heterocyclic group contains an —NH— moiety that nitrogen may be optionally substituted by a group selected from $R^8$;

D is —C(O)—, —N($R^9$)C(O)—, —S(O)$_2$—, —NS(O)$_2$—, —OC(O)— or D is a direct bond;

$R^5$ is $C_{1-6}$alkyl, $C_{2-6}$alkenyl, $C_{2-6}$alkynyl, $C_{3-6}$cycloalkyl, phenyl, naphthyl or a heterocyclic group, wherein in $R^5$ any $C_{1-6}$alkyl, $C_{2-6}$alkenyl, $C_{2-6}$alkynyl, $C_{3-6}$cycloalkyl, phenyl, naphthyl or heterocyclic groups (on a ring carbon) may be optionally substituted by one or more $R^6$ and if said heterocyclic group contains an —NH— moiety that nitrogen may be optionally substituted by a group selected from $R^8$;

E is —O—, —N($R^9$)—, —C(O)—, —N($R^9$)C(O)—, —C(O)N($R^9$)—, —S(O)$_a$— wherein a is 0–2, —OC(O)—, —C(O)O—, —N($R^9$)C(O)O—, —OC(O)N($R^9$)—, —C(S)N($R^9$)—, —N($R^9$)C(S)—, —SO$_2$N($R^9$)—, —N($R^9$)SO$_2$—, —N($R^9$)C(O)N($R^9$)—, —N($R^9$)C(S)N($R^9$)—, —SO$_2$NHC(O)—, —SO$_2$N($R^9$)C(O)—, —C(O)NHSO$_2$— or E is a direct bond;

$R^6$ is trifluoromethyl, $C_{1-6}$alkyl, halo, hydroxy, trifluoromethoxy, cyano, $C_{1-6}$alkoxy, formyl, $C_{1-6}$alkanoyl, $C_{1-6}$alkanoyloxy, amino, N-($C_{1-6}$alkyl)amino, N-($C_{1-6}$alkyl)$_2$amino, $C_{1-6}$alkanoylamino, $C_{1-6}$alkanoyl(N-$C_{1-6}$alkyl)amino, nitro, carboxy, carbamoyl, $C_{1-6}$alkoxycarbonyl, thiol, $C_{1-6}$alkylsulphanyl, $C_{1-6}$alkylsulphinyl, $C_{1-6}$alkylsulphonyl, $C_{1-6}$alkylsulphonylamino, sulphamoyl, N-($C_{1-6}$alkyl)aminosulphonyl, N-($C_{1-6}$alkyl)$_2$aminosulphonyl, N-($C_{1-6}$alkyl)carbamoyl, N-($C_{1-6}$alkyl)$_2$carbamoyl, ureido, N'-($C_{1-6}$alkyl)ureido or N'-($C_{1-6}$-alkyl)$_2$ureido, $C_{2-6}$alkenyl, $C_{2-6}$alkynyl or $C_{3-6}$cycloalkyl, naphthyl, phenyl or a heterocyclic group wherein in $R^6$ any $C_{1-6}$alkyl, $C_{2-6}$alkenyl, $C_{2-6}$alkynyl, $C_{3-6}$cycloalkyl, naphthyl, phenyl or heterocyclic groups (on a ring carbon) may be optionally substituted by one or more $R^7$ and if said heterocyclic group contains an —NH— moiety that nitrogen may be optionally substituted by a group selected from $R^8$;

$R^7$ is trifluoromethyl, cyano, $C_{1-6}$alkyl, halo, hydroxy, trifluoromethoxy, $C_{1-6}$alkoxy, formyl, $C_{1-6}$alkanoyl, $C_{1-6}$-alkanoyloxy, amino, N-($C_{1-6}$alkyl) amino, N-($C_{1-6}$alkyl)$_2$amino, $C_{1-6}$alkanoylamino, $C_{1-6}$alkanoyl(N-$C_{1-6}$alkyl)amino, nitro, carboxy, carbamoyl, $C_{1-6}$alkoxycarbonyl, thiol, $C_{1-6}$alkylsulphanyl, $C_{1-6}$alkylsulphinyl, $C_{1-6}$alkylsulphonyl, $C_{1-6}$alkylsulphonylamino, sulphamoyl, N-($C_{1-6}$alkyl)aminosulphonyl, N-($C_{1-6}$alkyl)$_2$aminosulphonyl, N-($C_{1-6}$alkyl)carbamoyl, N-($C_{1-6}$alkyl)$_2$carbamoyl, $C_{2-6}$alkenyl, $C_{2-6}$alkynyl, $C_{3-6}$cycloalkyl or a heterocyclic group (optionally substituted by one or more $R^{11}$), and wherein $R^7$ any $C_{1-6}$alkyl, $C_{2-6}$alkenyl, $C_{2-6}$alkynyl or $C_{3-6}$cycloalkyl groups may be optionally substituted by one or more groups selected from $R^{12}$;

$R^8$ is $C_{1-6}$alkyl, $C_{1-6}$alkanoyl, $C_{1-6}$alkylsulphonyl, $C_{1-6}$alkoxycarbonyl, carbamoyl, N-($C_{1-6}$alkyl) carbamoyl, N,N-($C_{1-6}$alkyl)$_2$carbamoyl, benzoyl, (heterocyclic group)carbonyl, phenylsulphonyl, (heterocyclic group)sulphonyl, phenyl or a carbon linked heterocyclic group, and wherein in $R^8$ any $C_{1-6}$alkyl, phenyl or heterocyclic group (on a ring carbon) may be optionally substituted by one or more $R^6$, and if a heterocyclic group contains an —NH— moiety that nitrogen may be optionally substituted by a group selected from $R^{11}$;

$R^9$ is hydrogen or $C_{1-6}$alkyl optionally substituted by one or more $R^{10}$ with the proviso that $R^{10}$ is not a substituent on the carbon attached to a nitrogen atom;

$R^{10}$ is halo, hydroxy, amino, cyano, nitro, trifluoromethyl, trifluoromethoxy, $C_{1-6}$alkyl, $C_{2-6}$alkenyl, $C_{2-6}$alkynyl, N-($C_{1-6}$alkyl)amino, N-($C_{1-6}$alkyl)$_2$amino, $C_{1-6}$-alkanoylamino, $C_{1-6}$alkanoyl(N-$C_{1-6}$alkyl)amino, $C_{1-6}$alkylsulphonylamino, $C_{1-6}$alkylsulphonyl (N-$C_{1-6}$alkyl)amino, thiol, $C_{1-6}$alkylsulphanyl, $C_{1-6}$alkylsulphinyl, $C_{1-6}$alkylsulphonyl, sulphamoyl, N-($C_{1-6}$alkyl)aminosulphonyl, N-($C_{1-6}$alkyl)$_2$aminosulphonyl, carboxy, carbamoyl, N-($C_{1-6}$alkyl)carbamoyl, N-($C_{1-6}$alkyl)$_2$carbamoyl, $C_{1-6}$alkoxycarbonyl, $C_{1-6}$alkanoyl or formyl;

$R^{11}$ is $C_{1-6}$alkyl, $C_{1-6}$alkanoyl, $C_{1-6}$alkylsulphonyl, $C_{1-6}$alkoxycarbonyl, carbamoyl, N-($C_{1-6}$alkyl) carbamoyl, N,N-($C_{1-6}$alkyl)$_2$carbamoyl, $C_{1-6}$alkoxy $C_{1-6}$alkanoyl, phenyl$C_{1-6}$alkyl, benzoyl, phenyl$C_{1-6}$alkanoyl, phenyl$C_{1-6}$alkoxycarbonyl or phenylsulphonyl and wherein in $R^{11}$ and $C_{1-6}$alkyl group can be optionally substituted by one or more $R^{13}$;

$R^{12}$ is halo, hydroxy, N-methylpiperazinyl, N-acetylpiperazinyl, morpholino, piperidino, cyano, amino, N,N-dimethylamino, acetamido, carbamoyl, carboxy, methanesulfphonyl or sulphamoyl;

$R^{13}$ is halo, hydroxy, cyano, amino, N,N-dimethylamino, acetamido, carbamoyl, carboxy, methanesulphonyl or sulphamoyl;

n is 0–5; wherein the values of $R^3$ may be the same or different;

or a pharmaceutically acceptable salt or an in vivo hydrolysable ester thereof; with the proviso that if $R^1$ is methyl, $R^2$ is trifluoromethyl and Ring A is piperazin-1-yl then $(R^3)_n$ is not i) 4-cyanobenzoyl, ii) 2-methyl-4-benzyloxycarbonyl, iii) 2-methyl, iv) 2-methyl-4-cyanobenzoyl, v) 2,5-dimethyl-4-benzyl, vi) 2,5-dimethyl or vii) 2,5-dimethyl-4-cyanobenzoyl.

In this specification the term "alkyl" includes both straight and branched chain alkyl groups but references to individual alkyl groups such as "propyl" are specific for the straight chain version only. For example, "$C_{1-6}$alkyl" includes $C_{1-4}$alkyl, methyl, ethyl, propyl, isopropyl and t-butyl. However, references to individual alkyl groups such as 'propyl' are specific for the straight chained version only and references to individual branched chain alkyl groups such as 'isopropyl' are specific for the branched chain version only. The term "halo" refers to fluoro, chloro, bromo and iodo. Where a phrase such as "any $C_{1-6}$alkyl groups may be optionally substituted by one or more groups" for the avoidance of doubt, is to be understood that this refers to all groups that contain a $C_{1-6}$alkyl group, for example this phrase would also relate to a $C_{1-6}$alkanoyl group if that was listed in the paragraph.

A "nitrogen linked mono or bicyclic heterocyclic ring" is a saturated, partially saturated or fully unsaturated, mono or bicyclic ring containing 4–12 atoms, one atom of which is a nitrogen atom (attached to form an amide as shown) and the other atoms are either all carbon atoms or they are carbon atoms and 1–3 heteroatoms chosen from nitrogen, sulphur or oxygen, wherein a —CH$_2$— group can optionally be replaced by a —C(O)— and a ring nitrogen and/or sulphur atom may be optionally oxidised to form the N-oxide and or the S-oxides. It will be appreciated that in forming this nitrogen link, the nitrogen atom is not quaternised, i.e. a neutral compound is formed.

A "heterocyclic group" is a saturated, partially saturated or unsaturated, mono or bicyclic ring containing 4–12 atoms of which at least one atom is chosen from nitrogen, sulphur or oxygen, which may, unless otherwise specified, be carbon or nitrogen linked, wherein a —$CH_2$— group can optionally be replaced by a —C(O)— and a ring nitrogen and/or sulphur atom may be optionally oxidised to form the N-oxide and or the S-oxides. Suitable values for a "heterocyclic group" include morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, tetrahydropyranyl, imidazolyl, pyrimidyl, pyrazinyl, pyridazinyl, isoxazolyl, 4-pyridone, 1-isoquinolone, 2-pyrrolidone, 4-thiazolidone, pyridine-N-oxide and quinoline-N-oxide.

An example of "$C_{1-6}$alkanoyloxy" is acetoxy. Examples of "$C_{1-6}$alkoxycarbonyl" include methoxycarbonyl, ethoxycarbonyl, n- and t-butoxycarbonyl. Examples of "$C_{1-6}$alkoxy" include methoxy, ethoxy and propoxy. Examples of "$C_{1-6}$alkanoylamino" include formamido, acetamido and propionylamino. Examples of "$C_{1-6}$alkylsulphanyl" include methylthio and ethylthio. Examples of "$C_{1-6}$alkylsulphinyl" include methylsulphinyl and ethylsulphinyl. Examples of "$C_{1-6}$alkylsulphonyl" include $C_{1-6}$alkylsulphonyl, mesyl and ethylsulphonyl. Examples of "$C_{1-6}$alkylsulphonylamino" include $C_{1-4}$alkylsulphonylamino, mesylamino and ethylsulphonylamino. Examples of "$C_{1-6}$alkanoyl" include $C_{1-4}$alkanoyl, propionyl and acetyl. Examples of "N-($C_{1-6}$alkyl)amino" include methylamino and ethylamino. Examples of "N-($C_{1-6}$alkyl)$_2$amino" include di-N-methylamino, di-(N-ethyl)amino and N-ethyl-N-methylamino. Examples of "$C_{3-6}$cycloalkyl" are cyclopropyl and cyclohexyl. Examples of "$C_{2-6}$alkenyl" are $C_{2-4}$alkenyl, vinyl, allyl and 1-propenyl. Examples of "$C_{2-6}$alkynyl" are $C_{2-4}$alkynyl, ethynyl, 1-propynyl and 2-propynyl. Examples of "$C_{1-6}$alkanoyl(N-$C_{1-6}$alkyl) amino" are $C_{1-4}$alkanoyl(N-$C_{1-4}$alkyl)amino, (N-methyl) formamido and (N-propyl)acetamido. Examples of "N-($C_{1-6}$alkyl)aminosulphonyl" are N-($C_{1-4}$alkyl)aminosulphonyl, N-(methyl)aminosulphonyl and N-(ethyl)aminosulphonyl. Examples of "N-($C_{1-6}$alkyl)$_2$aminosulphonyl" are N-($C_{1-4}$alkyl)$_2$aminosulphonyl, N-(dimethyl)aminosulphonyl and N-(methyl)-N-(ethyl)aminosulphonyl. Examples of "N-($C_{1-6}$alkyl)carbamoyl" are N-($C_{1-4}$alkyl)carbamoyl, methylaminocarbonyl and ethylaminocarbonyl. Examples of "N-($C_{1-6}$alkyl)$_2$carbamoyl" are N-($C_{1-4}$alkyl)$_2$carbamoyl, dimethylaminocarbonyl and N-methyl-N-ethylaminocarbonyl. Examples of "(heterocyclic group) carbonyl" are pyrid-3-ylcarbonyl and pyrimid-2-ylcarbonyl. Examples of "(heterocyclic group)sulphonyl" are pyrid-3-ylsulphonyl and pyrimid-2-ylsulphonyl. Examples of "$C_{1-6}$alkoxy$C_{1-6}$alkanoyl" include ethoxypropionyl and methoxyacetyl. Examples of "phenyl$C_{1-6}$alkyl" include phenethyl and benzyl. Examples of "phenyl$C_{1-6}$alkanoyl" include 3-phenylpropionyl and phenacetyl. Examples of "phenyl$C_{1-6}$alkoxycarbonyl" include benzyloxyoxycarbonyl and 2-phenylethoxycarbonyl. Examples of "N'-($C_{1-6}$alkyl)ureido" are N'-methylureido and N'-ethylureido. Examples of "N'-($C_{1-4}$alkyl)$_2$ureido" are N',N'-dimethylureido and N'-methyl-N'-ethylureido.

Preferred values of Ring A, $R^1$, $R^2$, $R^3$ and n are as follows. Such values may be used where appropriate with any of the definitions, claims or embodiments defined hereinbefore or hereinafter.

Preferably Ring A is the morpholino, piperidyl, piperazinyl, pyrrolidinyl, thiomorpholino, pyrrolinyl, homopiperazinyl, pyrrolyl, pyrazolyl, pyrazolinyl, imidazolyl, imidazolinyl, imidazolidinyl, pyrazolidinyl, indolyl, isoindolyl, isoindolinyl, indolinyl, benzimidazolyl, purinyl, 1,2,3,4-4H-isoquinolinyl and triazolyl wherein if any of these rings contain an —NH— moiety that nitrogen is substituted by $R^4$—D—.

More preferably Ring A is piperidinyl, pyrrolidinyl, pyrrolinyl, homopiperazinyl, indolinyl, 1,2,3,4-4H-isoquinolinyl and isoindolinyl.

Particular Ring A is piperidiyl, piperazinyl, pyrrolidinyl, pyrrolinyl, indolinyl, 1,2,3,4-4H-isoquinolinyl and isoindolinyl.

More particularly Ring A is piperidyl, piperazinyl or indolinyl.

In one aspect of the invention preferably Ring A is piperazinyl.

In another aspect of the invention preferably Ring A is piperidyl, pyrrolidinyl, pyrrolinyl, indolinyl, 1,2,3,4-4H-isoquinolinyl and isoindolinyl.

In another aspect of the invention more preferably Ring A is piperidyl or indolinyl.

In a further aspect of the invention, preferably Ring A is piperidyl, piperazinyl or indolinyl; wherein said piperazinyl is optionally substituted on nitrogen by $R^4$—D—;

$R^4$ is $C_{1-4}$alkyl, phenyl {optionally substituted with one or more t-butyl, isopropyl, nitro, halo, N,N-dimethylcarbamoyl, N,N-dimethylamino, 2-hydroxyethylamino, cyano, acetyl, methoxy or carboxy} or thienyl; and D is —$SO_2$— or —C(O)—.

In one aspect of the invention $R^1$ and $R^2$ are independently $C_k$alkyl optionally substituted by from 1 to 2k+1 atoms selected from fluoro and chloro wherein k is 1–3.

Preferably $R^1$ and $R^2$ are independently $C_k$alkyl optionally substituted by from 1 to 2k+1 atoms selected from fluoro and chloro, wherein k is 1–3.

or $R^1$ and $R^2$, together with the carbon atom to which they are attached, form a cyclopropane ring optionally substituted by from 1 to 4 fluorine atoms.

More preferably $R^1$ and $R^2$ are independently $C_k$alkyl optionally substituted by from 1 to 2k+1 fluorine atoms, wherein k is 1–2, or $R^1$ and $R^2$, together with the carbon atom to which they are attached, form a cyclopropane ring optionally substituted by from 1 to 4 fluorine atoms.

Particularly $R^1$ and $R^2$ are independently methyl, fluoromethyl, difluoromethyl, trifluoromethyl, 2,2,2-trifluoroethyl and perfluoroethyl, or $R^1$ and $R^2$, together with the carbon atom to which they are attached, form a cyclopropane ring optionally substituted by from 1 to 4 fluorine atoms.

More particularly $R^1$ and $R^2$ are independently methyl, fluoromethyl, difluoromethyl and trifluoromethyl, or $R^1$ and $R^2$, together with the carbon atom to which they are attached, form a cyclopropane ring optionally substituted by from 1 to 4 fluorine atoms.

Preferred combinations of $R^1$ and $R^2$ are as follows.

Preferably $R^1$ and $R^2$ are both methyl or one of $R^1$ and $R^2$ is methyl and the other is trifluoromethyl.

More preferably one of $R^1$ and $R^2$ is methyl and the other is trifluoromethyl.

Preferably $R^4$ is $C_{1-4}$alkyl, phenyl or a heterocyclic group, wherein in $R^4$ any $C_{1-4}$alkyl, phenyl or a heterocyclic group (on a ring carbon) may be optionally substituted by one or more $R^6$ and if said heterocyclic group contains an —NH— moiety that nitrogen may be optionally substituted by a group selected from $R^8$.

More preferably $R^4$ is $C_{1-4}$alkyl {optionally substituted with one or more hydroxy, acetamido, methoxy, carbamoyl, N,N-dimethylcarbamoyl, N,N-dimethylamino or mesyl}, phenyl {optionally substituted with one or more halo, N,N-dimethylcarbamoyl, N,N-dimethylamino, 2-hydroxyethylamino, N-methylpiperazinyl, N-acetylpiperazinyl, N-mesylpiperazinyl, amino, methanesulphinyl, acetamido, mesyl} or a heterocyclic group {where if the heterocyclic group consists an —NH— moiety that nitrogen may be optionally substituted with methyl, mesyl or acetyl} which heterocyclic group may be optionally substituted with one or more methyl, halo, N,N-dimethylcarbamoyl, N,N-dimethylamino, 2-hydroxyethylamino, N-methylpiperazinyl, N-acetylpiperazinyl, N-mesylpiperazinyl, amino, methanesulphinyl, acetamido, methanesulphonyl.

Particularly $R^4$ is ethyl, 4-mesylphenyl, 4-methylthiophenyl, 4-carboxyphenyl, 4-(N,N-dimethylcarbamoyl)phenyl, 4-fluorophenyl, 4-(2-hydroxyethylamino)phenyl, 4-cyanophenyl, 2-chloro-4-cyanophenyl, 4-acetylphenyl, 4-methoxyphenyl, 4-(N,N-dimethylamino)phenyl, 4-bromophenyl or thien-2-yl.

In another aspect of the invention, more preferably $R^4$ is $C_{1-4}$alkyl, phenyl {optionally substituted with one or more t-butyl, isopropyl, nitro, halo, N,N-dimethylcarbamoyl, N,N-dimethylamino, 2-hydroxyethylamino, cyano, acetyl, methoxy or carboxy} or thienyl.

In an additional aspect of the invention, more preferably $R^4$ is phenyl optionally substituted with one or more halo, N,N-dimethylcarbamoyl, 2,-hydroxyethylamino, cyano, methoxy or carboxy.

Preferably D is —C(O)—, —N($R^9$)C(O)—, —S(O)$_2$— or —NS(O)$_2$— or D is a direct bond.

More preferably D is —N($R^9$)C(O)—, —S(O)$_2$— or —NS(O)$_2$— or D is a direct bond.

Particularly D is —SO$_2$— or —C(O)—.

Preferably $R^4$—D— is $C_{1-4}$alkylsulphonyl optionally substituted by one or more $R^6$, phenylsulphonyl optionally substituted by one or more $R^6$ or thienylsulphonyl optionally substituted by one or more $R^6$.

In another aspect of the invention preferably $R^4$—D— is $C_{1-4}$alkylsulphonyl optionally substituted by one or more $R^6$, phenylcarbonyl optionally substituted by one or more $R^6$, phenylsulphonyl optionally substituted by one or more $R^6$ or thienylsulphonyl optionally substituted by one or more $R^6$.

More preferably $R^4$—D— is ethylsulphonyl, 4-carboxyphenylsulphonyl, 4-(N,N-dimethylcarbamoyl)phenylsulphonyl, 4-fluorophenylsulphonyl or thien-2-ylsulphonyl.

In another aspect of the invention more preferably $R^4$—D— is ethylsulphonyl, 4-carboxyphenylsulphonyl, 4-(N,N-dimethylcarbamoyl)phenylsulphonyl, 4-fluorophenylsulphonyl, 4-fluorophenylcarbonyl or thein-2-ylsulphonyl.

In a further aspect of the invention more preferably $R^4$—D— is ethylsulphonyl, 4-carboxyphenylsulphonyl, 4-(N,N-dimethylcarbamoyl)phenylsulphonyl, 4-fluorophenylsulphonyl, 4-fluorobenzoyl, thien-2-ylsulphonyl, 4-(N,N-dimethylcarbamoyl)benzoyl, 4-(2-hydroxyethylamino)phenylsulphonyl, 4-cyanophenylsulphonyl, 2-chloro-4-cyanophenylsulphonyl, 4-acetylphenylsulphonyl, 4-methoxyphenylsulphonyl, 4-methoxybenzoyl, 4-(N,N-dimethylamino)benzoyl, 4-bromophenylsulphonyl or 4-bromobenzoyl.

In an additional aspect of the invention more preferably $R^4$—D— is ethylsulphonyl, 4-carboxyphenylsulphonyl, 4-(N,N-dimethylcarbamoyl)phenylsulphonyl, 4-fluorophenylsulphonyl, 4-fluorobenzoyl, thien-2-ylsulphonyl, 4-(N,N-dimethylcarbamoyl)benzoyl, 4-(2-hydroxyethylamino)phenylsulphonyl, 4-cyanophenylsulphonyl, 2-chloro-4-cyanophenylsulphonyl, 4-acetylphenylsulphonyl, 4-methoxyphenylsulphonyl, 4-methoxybenzoyl, 4-(N,N-dimethylamino)benzoyl, 4-bromophenylsulphonyl, 4-bromobenzoyl, 4-t-butylbenzoyl, 4-isopropylphenylsulphonyl or 2-nitrophenylsulphonyl.

In an additional aspect of the invention particularly $R^4$—D— is 4-carboxyphenylsulphonyl, 4-(N,N-dimethylcarbamoyl)phenylsulphonyl, 4-fluorophenylsulphonyl, 4-(2-hydroxyethylamino)phenylsulphonyl, 4-cyanophenylsulphonyl or 4-methoxyphenylsulphonyl.

Preferably $R^5$ is $C_{1-4}$alkyl, $C_{2-4}$alkenyl, $C_{2-4}$alkynyl, $C_{3-6}$cycloalkyl, phenyl or a heterocyclic group, wherein in $R^5$ any $C_{1-4}$alkyl, $C_{2-4}$alkenyl, $C_{2-4}$alkynyl, $C_{3-6}$cycloalkyl, phenyl or heterocyclic group (on a ring carbon) may be optionally substituted by one or more $R^6$ and if said heterocyclic group contains an —NH— moiety that nitrogen may be optionally substituted by a group selected from $R^8$.

More preferably $R^5$ is $C_{1-4}$alkyl, $C_{2-4}$alkenyl, $C_{2-4}$alkynyl, phenyl or a heterocyclic group, wherein in $R^5$ any $C_{1-4}$alkyl, $C_{2-4}$alkenyl, $C_{2-4}$alkynyl, phenyl or heterocyclic group (on a ring carbon) may be optionally substituted by one or more $R^6$ and if said heterocyclic group contains an —NH— moiety that nitrogen may be optionally substituted by a group selected from $R^8$.

More particularly $R^5$ is methyl, ethyl, ethenyl and ethynyl, a heterocyclic group {wherein if the heterocyclic group contains an —NH— moiety then that nitrogen may be optionally substituted with methyl, acetyl or mesyl} optionally substituted on a ring carbon by one or more methyl, halo, N,N-dimethylcarbamoyl, N,N-dimethylamino, 2-hydroxyethylamino, N-methylpiperazinyl, N-acetylpiperazinyl, N-mesylpiperazinyl, amino, methanesulphinyl, acetamido, methanesulphonyl and phenyl optionally substituted by one or more methyl, halo, N,N-dimethylcarbamoyl, N,N-dimethylamino, 2-hydroxyethylamino, N-methylpiperazinyl, N-acetylpiperazinyl, N-mesylpiperazinyl, amino, methanesulphinyl, acetamido, methanesulphonyl.

In a further aspect of the invention $R^4$ is 4-mesylphenyl, 4-methylthiophenyl, 4-fluorophenyl or 4-cyanophenyl.

Preferably E is —O—, —N($R^9$)—, —C(O)—, —N($R^9$)C(O)—, —C(O)N($R^9$)—, —S(O)$_a$— wherein a is 1 or 2, —OC(O)—, —C(O)O—, —N($R^9$)C(O)O—, —OC(O)N($R^9$)—, SO$_2$N($R^9$)—, —N($R^9$)SO$_2$—, —N($R^9$)C(O)N($R^9$)—, —SO$_2$NHC(O)—, —SO$_2$N($R^9$)C(O)— or —C(O)NHSO$_2$— or E is a direct bond.

More preferably E is —O—, —N($R^9$)—, —C(O)—, —N($R^9$)C(O)—, —C(O)N($R^9$)—, —S(O)$_a$— wherein a is 1 or 2, —SO$_2$N($R^9$)—, —N($R^9$)SO$_2$— or —N($R^9$)C(O)N($R^9$)— or E is a direct bond.

Particularly E is —N($R^9$)C(O)—, —C(O)N($R^9$)—, —S(O)$_a$— wherein a is 1 or 2, —SO$_2$N($R^9$)—, —N($R^9$)SO$_2$— or —N($R^9$)C(O)N($R^9$)— or E is a direct bond.

In another aspect of the invention E is —SO$_2$—, —S—, —C(O)— or —C(O)NH—.

Preferably $R^6$ is $C_{1-6}$alkyl, halo, hydroxy, amino, carboxy, $C_{1-6}$alkylsulphonyl, $C_{1-6}$alkylsulphonylamino, N-($C_{1-6}$alkyl)aminosulphonyl, N-($C_{1-6}$alkyl)$_2$carbamoyl or a heterocyclic group wherein in $R^6$ any $C_{1-6}$alkyl group may be optionally substituted by one or more $R^7$ and if said heterocyclic group contains an —NH— moiety that nitrogen may be optionally substituted by a group selected from $R^8$.

More preferably $R^6$ is $C_{1-4}$alkyl, halo, hydroxy, amino, carboxy, $C_{1-4}$alkylsulphenyl, $C_{1-4}$alkylsulphonylamino, N-($C_{1-4}$alkyl)aminosulphonyl, N-($C_{1-4}$alkyl)$_2$carbamoyl or a heterocyclic group wherein in $R^6$ any $C_{1-4}$alkyl group may be optionally substituted by one or more $R^7$ and if said heterocyclic group contains an —NH— moiety that nitrogen may be optionally substituted by a group selected from $R^8$.

Particularly $R^6$ is methyl, ethyl, 2-hydroxyethylamino, halo, hydroxy, amino, carboxy, mesyl, ethylsulphonyl, mesylamino, ethylsulphonylamino, N-methylaminosulphonyl, N-ethylaminosulphonyl, N-($C_{1-4}$alkyl)$_2$carbamoyl or a heterocyclic group wherein if said heterocyclic group contains —NH— moiety that nitrogen may be optionally substituted by a group selected from mesyl, methyl or acetyl.

Preferably $R^7$ is $C_{1-6}$alkyl, halo, hydroxy, amino, carboxy, $C_{1-6}$alkylsulphonyl, $C_{1-6}$alkylsulphonylamino, N-($C_{1-6}$alkyl)aminosulphonyl, N-($C_{1-6}$alkyl)$_2$carbamoyl or a heterocyclic group wherein in $R^7$ any $C_{1-6}$alkyl group may be optionally substituted by one or more $R^{12}$.

More preferably $R^7$ is $C_{1-4}$alkyl, halo, hydroxy, amino, carboxy, $C_{1-4}$alkylsulphonyl, $C_{1-4}$alkylsulphonylamino, N-($C_{1-4}$alkyl)aminosulphonyl, N-($C_{1-4}$alkyl)$_2$carbamoyl or a heterocyclic group wherein in $R^7$ any $C_{1-4}$alkyl group may be optionally substituted by one or more $R^{12}$.

Particularly $R^7$ is methyl, ethyl, 2-hydroxyethyl, halo, hydroxy, amino, carboxy, mesyl, ethylsulphonyl, mesylamino, ethylsulphonylamino, N-methylaminosulphonyl, N-ethylaminosulphonyl, N-($C_{1-4}$alkyl)$_2$carbamoyl or a heterocyclic group.

Preferably $R^8$ is $C_{1-6}$alkyl, $C_{1-6}$alkanoyl, $C_{1-6}$alkylsulphonyl, carbamoyl, N-($C_{1-6}$alkyl)carbamoyl or N,N-($C_{1-6}$alkyl)$_2$carbamoyl.

More preferably $R^8$ is $C_{1-4}$alkyl, $C_{1-4}$alkanoyl, $C_{1-4}$alkylsulphonyl, carbamoyl, N-($C_{1-4}$alkyl)carbamoyl or N,N-($C_{1-4}$alkyl)$_2$carbamoyl.

More preferably $R^8$ is methyl, ethyl, acetyl, mesyl, ethylsulphonyl, carbamoyl, N-methylcarbamoyl or N,N-dimethylcarbamoyl.

Preferably $R^9$ is hydrogen or $C_{1-4}$alkyl optionally substituted by one or more $R^{10}$ with the proviso that $R^{10}$ is not a substituent on the carbon attached to a nitrogen atom.

More preferably $R^9$ is hydrogen, methyl or ethyl optionally substituted by one or more $R^{10}$ with the proviso that $R^{10}$ is not a substituent on the carbon attached to a nitrogen atom.

Particularly $R^9$ is hydrogen.

In another aspect of the invention particularly $R^9$ is methyl.

Preferably $R^{10}$ is hydroxy.

Preferably $R^{11}$ is $C_{1-6}$alkyl, $C_{1-6}$alkanoyl or $C_{1-6}$alkylsulphonyl.

More preferably $R^{11}$ is $C_{1-4}$alkyl, $C_{1-4}$alkanoyl or $C_{1-4}$alkylsulphonyl.

Particularly $R^{11}$ is methyl, mesyl or acetyl.

Particularly $R^{12}$ is hydroxy.

Particularly $R^{13}$ is hydroxy.

In one aspect of the invention preferably n is 0.

In another aspect of the invention preferably n is 1.

In an additional aspect of the invention preferably n is 2.

In a further aspect of the invention preferably n is 3.

In a further additional aspect of the invention preferably n is 4.

Preferably n is 1–3.

More preferably n is 2 or 3.

In another aspect of the invention, preferably n is 0–3.

Preferably $R^3$ is phenylsulphonyl optionally substituted by $R^6$, phenylthio optionally substituted by $R^6$, phenylcarbonyl optionally substituted by $R^6$ or $C_{1-4}$alkyl optionally substituted by $R^6$.

More preferably $R^3$ is 4-mesylphenylsulphonyl, 4-methylthiophenylthio, 4-fluorophenylcarbonyl or methyl.

In another aspect of the invention preferably $R^3$ is selected from amino, methyl, 4-mesylphenylsulphonyl, 4-methylthiophenylthio, 4-fluorobenzoyl and 4-cyanobenzoylamino.

Where —C(OH)($R^1$)($R^2$) represents a chiral center, the R-configuration is generally the preferred stereochemistry.

Therefore in a further aspect of the invention there is provided a compound of formula (I) (as depicted above) wherein:

Ring A is piperidyl, piperazinyl or indolinyl; wherein said piperazinyl is optionally substituted on nitrogen by $R^4$—D—;

One of $R^1$ and $R^2$ is methyl and the other is trifluoromethyl;

$R^3$ is a substituent on carbon and is selected from amino, methyl, 4-mesylphenylsulphonyl, 4-methylthiophenylthio, 4-fluorobenozyl and 4-cyanobenzoylamino;

$R^4$ is $C_{1-4}$alkyl, phenyl {optionally substituted with one or more t-butyl, isopropyl, nitro, halo, N,N-dimethylcarbamoyl, N,N-dimethylamino, 2-hydroxyethylamino, cyano, acetyl, methoxy or carboxy} or thienyl;

D is —$SO_2$— or —C(O)—; and n is 0 or 3;

or a pharmaceutically acceptable salt or an in vivo hydrolysable ester thereof.

Therefore in an additional aspect of the invention there is provided a compound of formula (I) (as depicted above) wherein:

Ring A is piperazinyl; wherein said piperazinyl is substituted on nitrogen by $R^4$—D—;

One of $R^1$ and $R^2$ is methyl and the other is trifluoromethyl;

$R^3$ is a substituent on carbon and is methyl;

$R^4$—D— is 4-carboxyphenylsulphinyl, 4-(N,N-dimethylcarbamoyl)phenylsulphonyl, 4-fluorophenylsulphonyl, 4-(2-hydroxyethylamino)phenylsulphonyl, 4-cyanophenylsulphonyl or 4-methoxyphenylsulphonyl;

n is 2;

or a pharmaceutically acceptable salt or an in vivo hydrolysable ester thereof.

Therefore in a further aspect of the invention there is provided a compound of formula (I'):

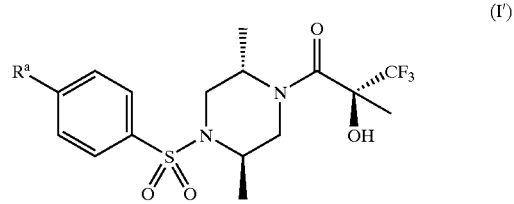

wherein:

$R^a$ is carboxy, N,N-dimethylcarbamoyl, fluoro, 2-hydroxyethylamino, cyano or methoxy;

or a pharmaceutically acceptable salt or an in vivo hydrolysable ester thereof.

A preferred compound of the invention is any one of the Examples or a pharmaceutically acceptable salt or an in vivo hydrolysable ester thereof.

Preferred compounds of the invention are Examples 4, 5, 6, 11, 12 and 15 or a pharmaceutically acceptable salt or an in vivo hydrolysable ester thereof.

Preferred aspects of the invention are those which relate to the compound or a pharmaceutically acceptable salt thereof.

Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which elevates PDH activity and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated by those skilled in the art that certain compounds of formula (I) contain one or more asymmetrically substituted carbon and/or sulphur atoms, and accordingly may exist in, and be isolated as enantiomerically pure, a mixture of diastereoisomer or as a racemate. It will also be appreciated by those skilled in the art that certain compounds of formula (I) contain substituents on a saturated heterocycle that may bear a syn- or anti- (or cis- and trans) relationship. It is to be understood that the present invention encompasses all such geometric isomers. Some compounds may exhibit polymorphism. It is to be understood that the present invention encompasses any racemic, optically-active, enantiomerically pure, mixture of diastereoisomers, polymorphic or stereoisomeric form, or mixtures thereof, which form possesses properties useful in the elevation of PDH activity, it being well known in the art how to prepare optically-active forms (for example, by resolution of the racemic form by recrystallization techniques, by synthesis from optically-active starting materials, by chiral synthesis, by enzymatic resolution, (for example WO 9738124), by biotransformation, or by chromatographic separation using a chiral stationary phase) and how to determine efficacy for the elevation of PDH activity by the standard tests described hereinafter.

It is also to be understood that certain compounds of the formula (I) and salts thereof can exist in solvated as well as unsolvated forms such as, for example, hydrated forms. It is to be understood that the invention encompasses all such solvated forms which elevate PDH activity.

A compound of the formula (I), or salt thereof, and other compounds of the invention (as hereinafter defined) may be prepared by any process known to be applicable to the preparation of chemically-related compounds. Such processes include, for example, those illustrated in European Patent Applications, Publication Nos. 0524781, 0617010, 0625516, and in GB 2278054, WO 9323358 and WO 9738124.

Another aspect of the present invention provides a process for preparing a compound of formula (I) or a pharmaceutically acceptable salt or an in vivo hydrolysable ester thereof, which process (in which variable groups are as defined for formula (I) unless otherwise stated) comprises of:

(a) deprotecting a protected compound of formula (II):

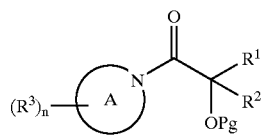

(II)

where Pg is an alcohol protecting group;

(b) coupling an amine of formula (III):

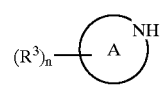

(III)

with an acid of formula (IV):

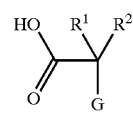

(IV)

wherein G is a hydroxyl group;

(c) coupling an amine of formula (III) with an activated acid derivative of formula (IV) wherein G is a hydroxyl group which may be protected as an ester or ether;

and thereafter if necessary:

i) converting a compound of the formula (I) into another compound of the formula (I);

ii) removing any protecting groups; or iii) forming a pharmaceutically acceptable salt or in vivo hydrolysable ester.

Suitable values for Pg are a benzyl group, a silyl group or an acetyl protecting group.

Specific conditions of the above reactions are as follows:

Process a)

Suitable reagents for deprotecting an alcohol of formula (II) are for example:

1) when Pg is benzyl:
   (i) hydrogen in the presence of palladium/carbon catalyst, i.e. hydrogenolysis; or
   (ii) hydrogen bromide or hydrogen iodide;

2) when Pg is a silyl protecting group:
   (i) tetrabutylammonium fluoride; or
   (ii) aqueous hydrofluoroic acid;

3) when Pg is acetyl:
   i) mild aqueous base for example lithium hydroxide; or
   ii) ammonia or an amine such as dimethylamine.

The reaction can be conducted in a suitable solvent such as ethanol, methanol, acetonitrile, or dimethylsulphoxide and may conveniently be performed at a temperature in the range of −40 to 100° C.

Compounds of formula (II) may be prepared according to the following scheme:

Scheme 1

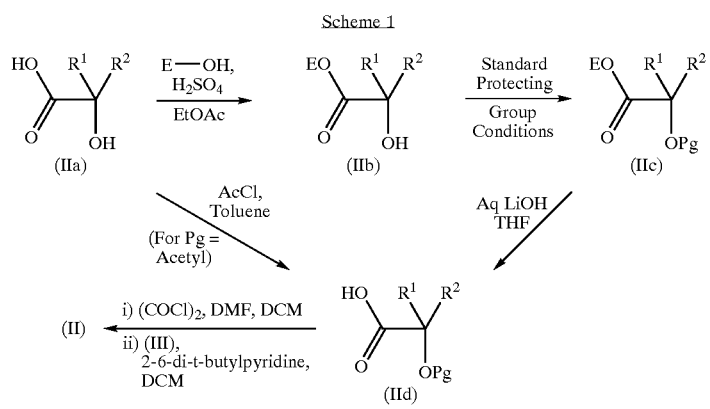

E is a carboxyl protecting group. Suitable values for E include $C_{1-6}$alkyl, such as methyl and ethyl.

Compounds of formula (IIa) and (IIIa) are commercially available compounds, or they are known in the literature, or they are prepared by standard processes known in the art.

Process b)

An amine of formula (III) and an acid of formula (IV) may be coupled together in the presence of a suitable coupling reagent. Standard peptide coupling reagents known in the art can be employed as suitable coupling reagents, for example conditions such as those described above for the coupling of (IId) and (III), or carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran, and dimethyl-formamide. The coupling reaction may conveniently be performed at a temperature in the range of −40 to 40° C.

Compounds of formula (IV) are commercially available compounds, or they are known in the literature, or they are prepared by standard processes known in the art.

If the resolved acid of formula (IV) is required it may be prepared by any of the known methods for preparation of optically-active forms (for example, by recrystallization of the chiral salt {for example WO 9738124}, by enzymatic resolution, by biotransformation, or by chromatographic separation using a chiral stationary phase). For example if an (R)-(+) resolved acid is required ti may be prepared by the method of Scheme 2 in World Patent Application Publication No. WO 9738124 for preparation of the (S)-(−) acid, i.e. using the classical resolution method described in European Patent Application Publication No. EP 0524781, also for preparation of the (S)-(−) acid, except that (1S,2R)-norephedrine may be used in place of (S)-(−)-1-phenylethylamine. The chiral acid may also be prepared by using the enzymatic resolution method as described in Tetrahedron Asymmetry, 1999, 10, 679.

Process c)

An amine of formula (III) may be coupled with an activated acid derivative of formula (IV) for example acid chlorides, acid anhydrides, or phenyl esters, wherein G is a hydroxyl group which may be suitably protected as a stable ester or ether. This coupling may be achieved optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran, and dimethyl-formamide. The coupling reaction may conveniently be performed at a temperature in the range of −40 to 40° C.;

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

For example, it will be appreciated that certain of the optional aromatic substituents in the compounds of the present invention may be introduced by standard aromatic substitution reactions or generated by conventional functional group modifications or interconversions either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminum trichloride) under Friedel Crafts conditions; the introduction of an alkyl group using an alkyl halide and Lewis acid (such as aluminium trichloride) under Freidel Crafts conditions; and the introduction of a halogeno group. Particular examples of modifications include the reduction of a nitro group to an amino group by, for example, catalytic hydrogenation with a nickel catalyst or treatment with iron in the presence of hydrochloric acid with heating; oxidation of alkylthio or alkylsulphinyl or alkyl-sulphonyl using, for example, hydrogen, peroxide in acetic acid with heating or 3-chloroperbenzoic acid. Particular examples of functional group interconversions are for example conversion of an aniline into a halophenyl by, for example, diazotisation in the presence of cupurous halides.

It is noted that many of the starting materials for synthetic methods as described above are commercially available and/or widely reported in the scientific literature, or could be made from commercially available compounds using adaptations of processes reported in the scientific literature.

It will also be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid such as, for example hydrochloric, sulphuric or phosphoric acid or trifluoroacetic acid and an arylmethoxycarbonyl group such as a benzyloxycarbonyl group may be removed, for example, by hydrogenation in the presence of a catalyst such as palladium-on-carbon, or by treatment with a Lewis acid for example boron tris(trifluoroacetate). A suitable alternative protecting group for a primary group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation in the presence of a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

In cases where compounds of formula (I) are sufficiently basic or acidic to form stable acid or basic salts, administration of the compound as a salt may be appropriate, and pharmaceutically acceptable salts may be made by conventional methods such as those described following. Examples of suitable pharmaceutically acceptable salts are organic acid addition salts formed with acids which form a physiologically acceptable anion, for example, tosylate, methanesulphonate, acetate, tartrate, citrate, succinate, benzoate, ascorbate, α-ketoglutarate, and α-glycerophosphate. Suitable inorganic salts may also be formed such as sulphate, nitrate, and hydrochloride.

Pharmaceutically acceptable salts may be obtained using standard procedures well known in the art, for example by reacting a sufficiently basic compound of formula (I) (or its ester) with a suitable acid affording a physiologically acceptable anion. It is also possible with most compounds of the invention to make a corresponding alkali metal (e.g. sodium, potassium, or lithium) or alkaline earth metal (e.g. calcium) salt by treating a compound of formula (I) (and in some cases the ester) with one equivalent of an alkali metal or alkaline earth metal hydroxide or alkoxide (e.g. the ethoxide or methoxide) in aqueous medium followed by conventional purification techniques.

The compounds of the formula (I) may be administered in the form of a prodrug which is broken down in the human or animal body to give a compound of the formula (I). Examples of prodrugs include in vivo hydrolysable esters of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable in vivo hydrolysable esters for a compound of the formula (I) containing a carboxy group include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methyoxycarbonyloxyethyl and may be formed at any carboxy group in the compounds of this invention.

Suitable in vivo hydrolysable esters of a compound of the formula (I) containing a hydroxy group includes inorganic esters such as phosphate esters and α-acyloxyalkyl ethers. Examples of α-acyloxyalkyl ethers include acetoxymethoxy and 2,2-dimethylpropyloxymethoxy. Other in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents for benzoyl include morpholino and piperazino linked from a ring nitrogen atom via a methylene group to the 3- or 4-position of the benzoyl ring.

In vivo cleavable prodrugs of compounds of formula (I) also include in vivo hydrolysable amides of compounds of the formula (I) containing a carboxy group, for example, a N-$C_{1-6}$alkyl or N-di-$C_{1-6}$alkyl amide such as N-methyl, N-ethyl, N-propyl, N-dimethyl, N-ethyl-N-methyl or N-dietyl amide.

The identification of compounds which elevate PDH activity is the subject of the present invention. These properties may be assessed, for example, using one or more of the procedures set out below:

(a) In vitro elevation of PDH activity

This assay determines the ability of a test compound to elevate PDH activity, cDNA encoding PDH kinase may be obtained by Polymerase Chain Reaction (PCR) and subsequent cloning. This may be expressed in a suitable expression system to obtain polypeptide with PDH kinase activity. For example rat PDHkinaseII (rPDHKII) obtained by expression of recombinant protein in *Eschericia coli* (*E. Coli*), was found to display PDH kinase activity.

In the case of the rPDHKII (Genbank accession number U10357) a 1.3 kb fragment encoding the protein was isolated by PCR from rat liver cDNA and cloned into a vector (for example pQE32—Quiagen Ltd.). The recombinant construct was transformed into *E. coli* (for example M15pRep4—Quiagen Ltd.). Recombinant clones were identified, plasmid DNA was isolated and subjected to DNA sequence analysis. One clone which had the expected nucleic acid sequence was selected for the expression work. Details of the methods for the assembly of recombinant DNA molecules and the expression of recombinant proteins in bacterial systems can be found in standard texts for example Sambrook et al, 1989, Molecular Cloning—A Laboratory Manual, $2^{nd}$ edition, Cold Spring Harbour Laboratory Press. Other known PDH kinases for use in assays, may be cloned and expressed in a similar manner.

For expression of rPDHKII activity, *E. coli* strain M15pRep4 cells were transformed with the pQE32 vector containing rPDHKII cDNA. This vector incorporates a 6-His tag onto the protein at its N-terminus. *E. coli* were grown to an optical density of 0.6 (600 nM) and protein expression was induced by the addition of 10 µM isopropylthio-β-galactosidase. Cells were grown for 18 hours at 18° C. and harvested by centrifugation. The resuspended cell paste was lysed by homogenisation and insoluble material removed by centrifugation at 2400× g for 1 hour. The 6-His tagged protein was removed from the supernatant using a nickel chelating nitrilotriacetic acid resin (Ni-NTA: Quiagen Ltd.) matrix (Quiagen) which was washed with 20 mM tris(hydroxymethyl)aminomethanehydrogen chloride, 20 mM imidazole, 0.5 M sodium chloride pH 8.0, prior to elution of bound protein using a buffer containing 20 mM tris(hydroxymethyl)aminomethanehydrogen chloride, 200 mM imidazole, 0.15 M sodium chloride pH 8.0. Eluted fractions containing 6-His protein were pooled and stored in aliquots at −80° C. in 10% glycerol.

Each new batch of stock enzyme was titrated in the assay to determine a concentration giving approximately 90% inhibition of PDH in the conditions of the assay. For a typical batch, stock enzyme was diluted to 7.5 µg/ml.

For assay of the activity of novel compounds, compounds were diluted with 10% dimethylsulphoxide (DMSO) and 10 µl transferred to individual wells of 96-well assay plates. Control wells contained 20 µl 10% DMSO instead of compound. 40 µl Buffer containing 50 mM potassium phosphate buffer pH 7.0, 10 mM ethylene glycol-bis(β-aminoethyl ether)-N,N-tetracetic acid (EGTA), 1 mM benzamidine, 1 mM phenylmethylsulphonyl fluoride (PMSF), 0.3 mM tosyl L-lysine chloromethyl ketone (TLCK), 2 mM dithiothreitol (DTT), recombinant rPDHKII and compounds were incubated in the presence of PDH kinase at room temperature for 45 minutes. In order to determine the maximum rate of the PDH reaction a second series of control wells were included containing 10% DMSO instead of compound and omitting rPDHKII. PDH kinase activity was then initiated by the addition of 5 µM ATP, 2 mM magnesium chloride and 0.04 U/ml PDH (porcine heart PDH Sigma P7032) in a total volume of 50 µl and plates incubated at ambient temperature for a further 45 minutes. The residual activity of the PDH was then determined by the additional of substrates (2.5 mM coenzyme A, 2.5 mM thiamine pyrophosphate (cocarboxylase), 2.5 mM sodium pyruvate, 6 mM NAD in a total volume of 80 µl and the plates incubated for 90 minutes at ambient temperature. The production of reduced NAD (NADH) was established by measured optical density at 340 nm using a plate reading spectrophotometer. The $ED_{50}$ for a test compound was determined in the usual way using results from 12 concentrations of the compound.

(b) In vitro elevation of PDH activity in isolated primary cells

This assay determines the ability of compounds to stimulate pyruvate oxidation in primary rat hepatocytes.

Hepatocytes were isolated by the two-step collagenase digestion procedure described by Seglen (Methods Cell Biol. (1976) 13, 29–33) and plated out in 6-well culture plates (Falcon Primaria) at 600000 variable cells per well in Dulbecco's Modified Eagles Medium (DMEM, Gibco BRL) containing 10% focal calf serum (FCS), 10% penicillin/streptomycin (Gibco BRL) and 10% non-essential amino acids (NEAAS, Gibco BRL). After 4 hours incubation at 37° C. in 5% $CO_2$, the medium was replaced with Minimum Essential Medium (MEM, Gibco BRL) containing NEAA and penicillin/streptomycin as above in addition to 10 nM dexamethasone and 10 nM insulin.

The following day cells were washed with phosphate buffered saline (PBS) and medium replaced with 1 ml HEPES-buffered Krebs solution (25 mM HEPES, 0.15M sodium chloride, 25 mM sodium hydrogen carbonate, 5 mM potassium chloride, 2 mM calcium chloride, 1 mM magnesium sulphate, 1 mM phosphate dihydrogen phosphate) containing the compound to be tested at the required concentration in 0.1% DMSO. Control wells contained 0.1% DMSO only and a maximum response was determined using a 10 µM treatment of a known active compound. After a precincubation period of 40 minutes at 37° C. in 5% $CO_2$, cells were pulsed with sodium pyruvate to a final concentration of 0.5 mM (containing $1-^{14}C$ sodium pyruvate (Amersham product CFA85) 0.18 Ci/mmol) for 12 minutes. The medium was then removed and transferred to a tube which was immediately sealed with a bung containing a suspended centre wall. Absorbent within the centre well was saturated with 50% phenylethylamine, and $CO_2$ in the medium released by the addition of 0.2 µl 60% (w/v) perchloric acid (PCA). Released $^{14}CO_2$ trapped in the absorbent was determined by liquid scintillation counting. The $ED_{50}$ for a test compound was determined in the usual way using results from 7 concentrations of the compound.

(c) In vivo elevation of PDH activity

The capacity of compounds to increase the activity of PDH in relevant tissues of rats may be measured using the test described hereinafter. Typically an increase in the proportion of PDH in its active, nonphosphorylated form may be detected in muscle, heart, liver and adipose tissue after a single administration of an active compound. This may be expected to lead to a decrease in blood glucose after repeated administration of the compound. For example a single administration of DCA, a compound known to activate PDH by inhibition of PDH kinase (Whitehouse, Cooper and Randle (1974) Biochem. J. 141, 761–774) 150 mg/kg, intraperitoneally, increased the proportion of PDH in its active form (Vary et al. (1988) Circ. Shock 24, 3–18) and after repeated administration resulted in a significant decrease in plasma glucose (Evans and Stacopole (1982) Biochem. Pharmacol. 31, 1295–1300).

Groups of rats (weight range 140–180 g) are treated with a single dose or multiple doses of the compound of interest by oral gavage in an appropriate vehicle. A control group of rats is treated with vehicle only. At a fixed time after the final administration of compound, animals are terminally anaesthetised, tissues are removed and frozen in liquid nitrogen. For determination of PDH activity, muscle samples are disrupted under liquid nitrogen prior to homogenisation by one thirty-second burst in a Polytron homogenizer in 4 volumes of a buffer containing 40 mM potassium phosphate pH 7.0, 5 mM EDTA, 2 mM DTT, 1% Triton X-100, 10 mM sodium pyruvate, 10 μM phenylmethylsulphonyl chloride (PMSF) and 2 μg/ml each of leupeptin, pepstain A and aprotinin. Extracts are centrifuged before assay. A portion of the extract is treated with PDH phosphatase prepared from pig hearts by the method of Siess and Wieland (Eur. J. Biochem (1972) 26, 96): 20 μl extract, 40 μl phosphatase (1:20 dilution), in a final volume of 125 μl containing 25 mM magnesium chloride, 1 mM calcium chloride. The activity of the untreated sample is compared with the activity of the dephosphorylated extract thus prepared. PDH activity is assayed by the method of Stansbie et al., (Biochem. J. (1976) 154, 225). 50 μl Extract is incubated with 0.75 mM NAD, 0.2 mM CoA, 1.5 mM thiamine pyrophosphate (TPP) and 1.5 mM sodium pyruvate in the presence of 20 μg/ml p-(p-amino-phenylazo)benzene sulphonic acid (AABS) and 50 mU/ml arylamine transferase (AAT) in a buffer containing 100 mM tris(hydroxymethyl)aminomethane, 0.5 mM EDTA, 50 mM sodium fluoride, 5 mM 2-mercaptoethanol and 1 mM magnesium chloride pH 7.8 AAT is prepared from pigeon livers by the method of Tabor et al. (J. Biol. Chem. (1953) 204, 127). The rate of acetyl CoA formation is determined by the rate of reduction of AABS which is indicated by a decrease in optical density at 460 nm.

Liver samples are prepared by an essentially similar method, except that sodium pyruvate is excluded from the extraction buffer and added to the phosphatase incubation to a final concentration of 5 mM.

Treatment of an animal with an active compound results in an increase in the activity of PDH complex in tissues. This is indicated by an increase in the amount of active PDH (determined by the activity of untreated extract as a percentage of the total PDH activity in the same extract after treatment with phosphatase).

According to a further aspect of the invention there is provided a pharmaceutical composition which comprises a compound of the formula (I) as defined hereinbefore or a pharmaceutically acceptable salt or an in vivo hydrolysable ester thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above composition may be prepared in a conventional manner using conventional excipients.

The compositions of the present invention are advantageously presented in unit dosage form. The compound will normally be administered to a warm-blooded animal at a unit dose within the range 5–5000 mg per square meter body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula (I) or a pharmaceutically acceptable salt or an in vivo hydrolysable ester thereof as defined hereinbefore for use in a method of treatment of the human or animal body by therapy.

We have found that compounds of the present invention elevate PDH activity and are therefore of interest for their blood glucose-lowering effects.

A further feature of the present invention is a compound of formula (I) and pharmaceutically acceptable salts or in vivo hydrolysable esters thereof for use as a medicament.

Conveniently this is a compound of formula (I), or a pharmaceutically acceptable salt or an in vivo hydrolysable ester thereof, for use as a medicament for producing an elevation of PDH activity in a warm-blooded animal such as a human being.

Particularly this is a compound of formula (I), or a pharmaceutically acceptable salt or an in vivo hydrolysable ester thereof, for use as a medicament for treating diabetes mellitus in a warm-blooded animal such as a human being.

In another aspect of the invention, particularly this is a compound of formula (I), or a pharmaceutically acceptable salt or an in vivo hydrolysable ester thereof, for use as a medicament for treating diabetes mellitus, peripheral vascular disease and myocardial ischaemia in a warm-blooded animal such as a human being.

Thus according to a further aspect of the invention there is provided the use of a compound of the formula (I), or a pharmaceutically acceptable salt or an in vivo hydrolysable ester thereof in the manufacture of a medicament for use in the production of an elevation of PDH activity in a warm-blooded animal such as a human being.

Thus according to a further aspect of the invention there is provided the use of a compound of the formula (I), or a pharmaceutically acceptable salt or an in vivo hydrolysable ester thereof in the manufacture of a medicament for use in the treatment of diabetes mellitus in a warm-blooded animal such as a human being.

Thus according to a further aspect of the invention there is provided the use of a compound of the formula (I), or a pharmaceutically acceptable salt or an in vivo hydrolysable ester thereof in the manufacture of a medicament for use in the treatment of diabetes mellitus, peripheral vascular disease and myocardial ischaemia in a warm-blooded animal such as a human being.

According to a further feature of the invention there is provided a method for producing an elevation of PDH activity in a warm-blooded animal, such as a human being, in need of such treatment which comprises administering to said animal an effective amount of a compound of formula (I) or a pharmaceutically acceptable salt or an in vivo hydrolysable ester thereof as defined hereinbefore.

According to a further feature of the invention there is provided a method of treating diabetes mellitus in a warm-blooded animal, such as a human being, in need of such treatment which comprises administering to said animal an effective amount of a compound of formula (I) or a pharmaceutically acceptable salt or an in vivo hydrolysable ester thereof as defined hereinbefore.

According to a further feature of the invention there is provided a method of treating diabetes mellitus, peripheral vascular disease and myocardial ischemia in a warm-blooded animal, such as a human being, in need of such treatment which comprises administering to said animal effective amount of a compound of formula (I) or a pharmaceutically acceptable salt or an in vivo hydrolysable ester thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The elevation of PDH activity described herein may be applied as a sole therapy or may involve, in addition to the subject of the present invention, one or more other substances and/or treatments. Such conjoint treatment may be achieved by way of the simultaneous, sequential or separate administration of the individual components of the treatment. For example in the treatment of diabetes mellitus chemotherapy may include the following main categories of treatment.

i) insulin;
ii) insulin secretagogue agents designed to stimulate insulin secretion (for example glibenclamide, tolbutamide, other sulphonylureas);
iii) oral hypoglycaemic agents such as metformin, thiazolidinediones;
iv) agents designed to reduce the absorption of glucose from the intestine (for example acarbose);
v) agents designed to treat complications of prolonged hyperglycacmia;
vi) other agents used to treat lactic acidaemia;
vii) inhibitors of fatty acid oxidation;
viii) lipid lowering agents;
ix) agents used to treat coronary heart disease and peripheral vascular disease such as aspirin, pentoxifylline, cilostazol; and/or
x) thiamine.

As stated above the compounds defined in the present invention are of interest for their ability to elevate the activity of PDH. Such compounds of the invention may therefore be useful in a range of disease states including diabetes mellitus, peripheral vascular disease, (including intermittent claudication), cardiac failure and certain cardiac myopathies, myocardial ischaemia, cerebral ischaemia and reperfusion, muscle weakness, hyperlipidaemias, Alzheimers disease and/or atherosclerosis. Alternatively such compounds of the invention may be useful in a range of disease states including peripheral vascular disease, (including intermittent claudication), cardiac failure and certain cardiac myopathies, myocardial ischaemia, cerebral ischaemia and reperfusion, muscle weakness, hyperlipidaemias, Alzheimers disease and/or atherosclerosis in particular peripheral vascular disease and myocardial ischaemia.

In addition to their use in therapeutic medicine, the compounds of formula (I) and their pharmaceutically acceptable salts are also useful as pharmacological tools in the development and standardisation of in vitro and in vivo test systems for the evaluation of the effects of elevators of PDH activity in laboratory animals such as cats, dogs, rabbits, monkeys, rats and mice, as part of the search for new therapeutic agents.

The invention will now be illustrated by the following non-limiting examples in which, unless stated otherwise:
(i) temperatures are given in degrees Celsius (° C.); operations were carried out at room or ambient temperature, that is, at a temperature in the range of 18–25° C.;
(ii) organic solutions were dried over anhydrous magnesium sulphate; evaporation of solvent was carried out using a rotary evaporator under reduced pressure (600–4000 Pascals; 4.5–30 mm Hg) with a bath temperature of up to 60° C.;
(iii) chromatography unless otherwise stated means flash chromatography on silica gel; thin layer chromatography (TLC) was carried out on silica gel plates; where a "Bond Elut" column is referred to, this means a column containing 10 g or 20 g of silica of 40 micron particle size, the silica being contained in a 60 ml disposable syringe and supported by a porous disc, obtained from Varian, Harbor City, Calif., USA under the name "Mega Bond Elut SI"
(iv) in general, the course of reactions was followed by TLC and reaction times are given for illustration only;
(v) yields are given for illustration only and are not necessarily those which can be obtained by diligent process development; preparations were repeated if more material was required;
(iv) when given, $^1$H NMR data is quoted and is in the form of delta values for major diagnostic protons, given in parts per million (ppm) relative to tetramethylsilane (TMS) as an internal standard, determined at 300 MHz using per-deuterio chloroform ($CDCl_3$) as the solvent unless otherwise stated; coupling constants (J) are given in Hz;
(vii) chemical symbols have their usual meanings; SI units and symbols are used;
(viii) solvent ratios are given in percentage by volume;
(ix) mass spectra (MS) were run with an electron energy of 70 electrons volts in the chemical ionisation (CI) mode using a direct exposure probe; where indicated ionisation was effected by electron impact (EI) or fast atom bombardment (FAB); where values for m/z are given, generally only ions which indicate the parent mass are reported, and unless otherwise stated the mass ion quoted is the negative mass ion—(M–H); and
(x) the following abbreviations are used:

| | |
|---|---|
| DMSO | dimethyl sulphoxide; |
| DMF | N-dimethylformamide; |
| DCM | dichloromethane; and |
| EtOAc | ethyl acetate; |

(xi) where (R) or (S) stereochemistry is quoted at the beginning of a name, unless further clarified, it is to be understood that the indicated stereochemistry refers to the —C(O)—C*(OH)($R^1$)$R^2$ centre as depicted in formula (I) (where C* is the chiral carbon); and
(xii) where a Biotage cartridge is referred to this means a cartridge containing KP-SIL™ silica, 60 Å particle size 32–63 μM, supplied by Biotage, a division of Dyax Corp., 1500 Avon Street Extended, Charlottesville, Va. 22902, USA;

EXAMPLE 1

(R)-[4-(4-Fluorobenzoyl)-1-(3,3,3-trifluoro-2-hydroxy-2-methylpropionyl)piperidine]

A solution of (S)-3,3,3-trifluoro-2-trimethylsilyoxy-2-methylpropanoyl chloride (J. Med. Chem., 1999, 42, 2741–2746) (293 mg, 1.2 mmol) in EtOAc (5 ml) was added to a stirred mixture of 4-(4-fluorobenzoyl)piperidine (207 mg, 1.0 mmol) and triethylamine (0.21 ml, 1.5 mmol) in EtOAc (25 ml). The resultant mixture was stirred at ambient temperature for 2 hours, washed with 1 M hydrochloric acid, saturated sodium hydrogen carbonate solution and brine, dried and evaporated. The residue was dissolved in methanol (10 ml), treated with 1 M hydrochloric acid (2 ml) and the mixture stirred at ambient temperature for 1 hour. The methanol was evaporated, the aqueous layer was extracted with EtOAc (2×25 ml), the EtOAc extracts were washed with saturated sodium hydrogen carbonate solution and brine, dried and evaporated. The residue was chromatographed on silica with 10% EtOA/DCM as eluent to give a solid which was recrystallized from EtOAc/hexane to give the title compound as a solid (104 mg, 0.3 mmol). Mp: 78–79° C.; NMR: 1.7 (s, 3H), 1.8–2.0 (m, 4H), 3.2 (dd, 2H), 3.5 (m, 1H), 4.4 (dd, 2H), 5.25 (s, 1H), 7.15 (dd, 2H), 8.0 (dd, 2H); m/z 346.

EXAMPLE 2

(R)-[(2S,5R)-2-Methyl-5-methyl-4-ethanesulphonyl-1-(3,3,3-trifluoro-2-hydroxy-2-methyl-propionyl)piperazine]

A solution of ethane sulphonyl chloride (91 mg, 0.707 mmol) in EtOAc (10 ml) was added to a stirred mixture of (R)-[(2S,5R)-2-methyl-1-(3,3,3-trifluoro-2-hydroxy-2-methylpropionyl)piperazine] (*J. Med. Chem.*, 1999, 42, 2741–2746) (150 mg, 0.59 mmol) and triethylamine (0.125 ml, 0.886 mmol) in EtOAc (15 ml). The resultant mixture was stirred at ambient temperature for 4 hours, washed with 1 M hydrochloric acid, saturated sodium hydrogen carbonate solution and brine, dried and evaporated. The residue was recrystallized from EtOAc/hexane to give the title compound as a solid (97 mg, 0.28 mmol). Mp: 142–144° C.; NMR: 1.15 (d, 3H), 1.3 (m, 6H), 1.65 (s, 3H), 2.9 (m, 2H), 3.3 (s, 1H), 3.35 (q, 2H), 4.05 (s, 1H), 4.15 (s, 1H), 4.4 (s, 1H), 4.7 (s, 1H); m/z 345.

EXAMPLE 3

(R)-[(2S,5R)-2-Methyl-5-methyl-4-(thien-2-ylsulphonyl)-1-(3,3,3-trifluoro-2-hydroxy-2-methylpropionyl)piperazine]

A solution of 2-thiophene sulphonyl chloride (129 mg, 0.707 mmol) in EtOAc (10 ml) was added to a stirred mixture of (R)-[(2S,5R)-2-methyl-5-methyl-1-(3,3,3-trifluoro-2-hydroxy-2-methylpropionyl)piperazine] (*J. Med. Chem.*, 1999, 42, 2741–2746) (150 mg, 0.59 mmol) and triethylamine (0.125 ml, 0.886 mmol) in EtOAc (15 ml). The resultant mixture was stirred at ambient temperature for 4 hours, washed with 1 M hydrochloric acid, saturated sodium hydrogen carbon solution and brine, dried and evaporated. The residue was recrystallized from EtOAc/hexane to give the title compound as a solid (71 mg, 0.18 mmol). Mp: 116–117° C.; NMR: 0.95 (d, 3H), 1.25 (dd, 3H), 1.65 (s, 3H), 3.2 (s, 3H), 3.3 (s, 1H), 3.5 (dd, 1H), 4.05 (s, 1H), 4.15 (s, 1H), 4.3 (s, 1H), 4.75 (s, 1H), 7.0 (dd, 1H), 7.5 (dd, 2H); m/z 399.

EXAMPLE 4

(R)-[(2S,5R)-2-Methyl-5-methyl-4-(4-carboxyphenylsulphonyl)-1-(3,3,3-trifluoro-2-hydroxy-2-methylpropionyl)piperazine]

A solution of 4-chlorosulphonyl benzoic acid (265 mg, 1.2 mmol) in EtOAc (10 ml) was added to a stirred mixture of (R)-[(2S,5R)-2-methyl-1-(3,3,3-trifluoro-2-hydroxy-2-methylpropionyl)piperazine (*J. Med. Chem.*, 1999, 42, 2741–2746) (254 mg, 1.0 mmol) and triethylamine (0.31 ml, 2.2 mmol) in EtOAc (15 ml). The resultant mixture was stirred at ambient temperature for 2 hours, washed with 1 M hydrochloric acid, brine, dried and evaporated. The residue was recrystallized from EtOAc/hexane to give the title compound as a solid (410 mg, 0.936 mmol). Mp: 194–196° C.; NMR: 0.9 (d, 3H), 1.2 (dd, 3H), 1.55 (s, 3H), 3.0 (dd, 1H), 3.15 (dd, 1H), 3.4 (s, 1H), 4.1 (m, 2H), 4.6 (s, 1H), 5.15 (s, 1H), 7.75 (d, 2H), 8.05 (d, 2H); m/z 437.

EXAMPLE 5

(R)-[(2S,5R)-2-Methyl-5-methyl-4-(4-dimethylcarbamoylphenylsulphonyl)-1-(3,3,3-trifluoro-2-hydroxy-2-methylpropionyl)piperazine]

Oxalyl chloride (0.08 ml, 0.88 mmol) was added to a solution of (R)-[(2S,5R)-2-methyl-5-methyl-4-(4-carboxyphenylsulphonyl)-1-(3,3,3-trifluoro-2-hydroxy-2-methylpropionyl)piperazine] (320 mg, 0.73 mmol) (Example 4) in DCM (25 ml). The resultant mixture was stirred at ambient temperature for 4 hours, evaporated to dryness, the residue treated with 40% aqueous dimethylamine (0.82 ml, 7.3 mmol) and the resultant mixture was stirred at ambient temperature overnight. The mixture was treated with EtOAc (25 ml), washed with 1 M hydrochloric acid, saturated sodium hydrogen carbonate solution and brine, dried and evaporated. The residue was chromatographed on silica with 50% EtOAc in DCM as eluent to give a solid which was recrystallized from EtOAc/hexane to give the title compound as a solid (26 mg, 0.056 mmol). Mp: 86–87° C.; NMR: 0.95 (d, 3H), 1.25 (dd, 3H), 1.65 (s, 3H), 2.95 (s, 3H), 3.1 (s, 3H), 3.25 (dd, 1H), 3.5 (dd, 1H), 4.2 (m, 2H), 4.5 (s, 1H), 4.8 (s, 1H), 7.5 (d, 2H), 7.85 (d, 2H); m/z: 464.

EXAMPLE 6

(R)-[(2S,5R)-2-Methyl-5-methyl-4-(4-fluorophenylsulphonyl)-1-(3,3,3-trifluoro-2-hydroxy-2-methylpropionyl)piperazine]

A solution of 4-fluorobenzene sulphonyl chloride (234 mg, 1.2 mmol) in EtOAc (10 ml) was added to a stirred mixture of (R)-[(2S,5R)-2-methyl-5-methyl-1-(3,3,3-trifluoro-2-hydroxy-2-methylpropionyl)piperazine] (*J. Med. Chem.*, 1999, 42, 2741–2746) (254 mg, 1.0 mmol) and triethylamine (0.17 ml, 1.2 mmol) in EtOAc (15 ml). The resultant mixture was stirred at ambient temperature for 2 hours, washed with 1 M hydrochloric acid, saturated sodium hydrogen carbonate solution and brine, dried and evaporated. The residue was recrystallized from EtOAc/hexane to give the title compound as a solid (230 mg, 0.56 mmol). Mp: 174–175° C.; NMR: 0.95 (d, 3H), 1.25 (d, 3H), 1.75 (s, 3H), 3.25 (dd, 1H), 3.35 (d, 1H), 3.5 (dd, 1H), 4.15 (m, 2H), 4.3 (s, 1H), 4.75 (s, 1H), 7.2 (d, 2H), 7.8 (d, 2H); m/z 411.

EXAMPLE 7

(R)-[(2S,5R)-2-Methyl-5-methyl-4-(4-fluorobenzoyl)-1-(3,3,3-trifluoro-2-hydroxy-2-methylpropionyl)piperazine]

A solution of 4-fluorobenzoyl chloride (190 mg, 1.2 mmol) in EtOAc (10 ml) was added to a stirred mixture of (R)-[(2S,5R)-2-methyl-1-(3,3,3-trifluoro-2-hydroxy-2-methylpropionyl)piperazine] (*J. Med. Chem.*, 1999, 42, 2741–2746) (254 mg, 1.0 mmol) and triethylamine (0.17 ml, 1.2 mmol) in EtOAc (15 ml). The resultant mixture was stirred at ambient temperature for 2 hours, washed with 1 M hydrochloric acid, saturated sodium hydrogen carbonate solution and brine, dried and evaporated. The residue was chromatographed on silica with 20% EtOAc in DCM as eluent to give the title compound as a solid which was recrystallized from EtOAc/hexane (290 mg, 0.77 mmol). Mp: 177–178° C.; NMR: 1.25 (d, 6H), 1.75 (s, 3H), 3.4 (m, 3H), 4.0 (m, 1H), 4.2 (m, 1H), 4.5 (s, 1H), 4.75 (s, 1H), 7.2 (d, 2H), 7.8 (d, 2H); m/z: 375.

EXAMPLE 8

(R)-[5-(4-Methylsulphanylphenylsulphanyl)-1-(3,3,3-trifluoro-2-hydroxy-2-methylpropionyl)indoline]

Oxalyl chloride (0.35 ml, 4.0 mmol) was added to a stirred suspension of (R)-(+)-2-hydroxy-2-methyl-3,3,3-trifluoropropanoic acid (0.58 g, 3.7 mmol) (Method A) in DCM (10 ml) containing DMF (1 drop). The mixture was stirred at ambient temperature for 18 hours and was then added to a solution of 5-(4-methylsulphanylphenylsulphanyl)indoline (1.03 g) (Method B) and 2,6-diphenylyridine (0.84 g, 3.64 mmol) in DCM (20 ml). The mixture was stirred for 16 hours, volatile material was removed by evaporation, and the residue was purified by flash column chromatography on silica gel eluting with 10–20% EtOAc/iso-hexane to give the title compound (0.935 g, 2.3 mmol) as a solid. NMR: 1.80 (s, 3H), 2.50 (s, 3H), 3.11–3.19 (m, 2H), 4.19–4.29 (m, 1H), 4.38–4.47 (m, 1H), 4.86 (s, 1H), 7.19–7.27 (m, 6H), 8.20 (d, 1H); m/z (+ve ESP): 414 (M+H)$^+$.

EXAMPLE 9

(R)-[5-(4-Mesylphenylsulphonyl)-1-(3,3,3-trifluoro-2-hydroxy-2-methylpropionyl)indoline]

Hydrogen peroxide (5 ml of a 30 wt. % solution in water) was added to a solution of (R)-[5-(4-methylsulphanylphenylsulphanyl)-1-(3,3,3-trifluoro-2-hydroxy-2-methylpropionyl)indoline] (0.53 mg, 1.3 mmol) (Example 8) in glacial acetic acid (10 ml) and the mixture was heated at 95° C. for 1 hour. The reaction mixture was allowed to cool to room temperature, EtOAc (150 ml) was added and the mixture was washed with saturated aqueous sodium hydrogen carbonate solution (2×150 ml) and brine (150 ml) and dried. Volatile material was removed by evaporation and the residue was purified on a silica gel Mega Bond Elut column eluting with 0–60% EtOAc/iso-hexane to give the title compound (0.42 g, 0.88 mmol) as a white solid. NMR (DMSO): 1.61 (s, 3H), 3.16–3.22 (m, 2H), 3.29 (s, 3H), 4.34–4.55 (m, 2H), 7.33 (s, 1H), 7.86–7.90 (m, 2H), 8.12–8.25 (m, 5H); m/z 476.

EXAMPLE 10

(R)-[(2S,5R)-2-Methyl-5-methyl-4-(4-dimethylcarbamoylbezoyl)-1-(3,3,3-trifluoro-2-hydroxy-2-methylpropionyl)piperazine]

To a stirred solution of (R)-[(2S,5R)-2-methyl-5-methyl-1-(3,3,3-trifluoro-2-hydroxy-2-methylpropionyl)piperazine] (J. Med. Chem., 1999, 42, 2741–2746) (400 mg, 1.57 mmol) and triethylamine (0.4 ml, 2.84 mmol) in EtOAc (25 ml) was added a solution of 4-dimethylcarbamoylbenzoyl chloride (350 mg, 1.66 mmol) in EtOAc (25 ml). The resultant mixture was stirred at ambient temperature for 24 hours, washed with 1 M hydrochloric acid, saturated sodium hydrogen carbonate solution and brine, dried and evaporated. The residue was chromatographed on silica with EtOAc as eluent to give the title compound as a solid (120 mg, 0.28 mmol). NMR: 1.1–1.13 (m, 6H), 1.6 (s, 3H), 2.9 (s, 3H), 3.1 (s, 3H), 3.25 (m, 1H), 3.4 (m, 1H), 4.25 (s, 2H), 4.65 (s, 1H), 4.9 (s, 1H), 5.2 (s, 1H), 7.3–7.4 (dd, 4H); m/z 428.

EXAMPLE 11

(R)-{(2S,5R)-2-Methyl-5-methyl-4-[4-(2-hydroxyethylamino)phenylsulphonyl]-1-(3,3,3-trifluoro-2-hydroxy-2-methylpropionyl)piperazine}

To a solution of (R)-[(2S,5R)-2-methyl-5-methyl-5-methyl-4-(4-fluorophenylsulphonyl)-1-(3,3,3-trifluoro-2-hydroxy-2-methylpropionyl)piperazine] (Example 6, 350 mg, 0.85 mmol) in 1-methyl-2-pyrrolidone (2 ml) was added ethanolamine (114 mg, 1.87 mmol) and the mixture heated at 120° C. for 24 hours. The mixture was cooled to ambient temperature, poured onto saturated ammonium chloride solution (30 ml), the mixture extracted with diethyl ether (2×30 ml), the combined ether extracts washed with brine, dried and evaporated. The residue was chromatographed on silica with EtOAc as eluent to give the title compound as a solid (143 mg, 0.32 mmol). NMR: 0.95 (d, 3H), 1.55 (d, 3H), 1.6 (s, 3H), 3.1 (m, 2H), 3.3 (dt, 2H), 3.4 (d, 1H), 3.8 (dt, 2H), 4.2 (s, 1H), 4.6 (m, 2H), 6.6 (d, 2H), 7.5 (d, 2H); m/z 411.

EXAMPLE 12

(R)-[(2S,5R)-2-Methyl-5-methyl-4-(4-cyanophenylsulphonyl)-1-(3,3,3-trifluoro-2-hydroxy-2-methylpropionyl)piperazine]

To a stirred solution of (R)-[(2S,5R)-2-methyl-5-methyl-1-(3,3,3-trifluoro-2-hydroxy-2-methylpropionyl)piperazine] (J. Med. Chem., 1999, 42, 2741–2746) (254 mg, 1.0 mmol) and triethylamine (0.17 ml, 1.2 mmol) in EtOAc (15 ml) was added a solution of 4-cyanobenzene sulphonyl chloride (220 mg, 1.1 mmol) in EtOAc (10 ml). The resultant mixture was stirred at ambient temperature for 2 hours, washed with 1 M hydrochloric acid, saturated sodium hydrogen carbonate solution and brine, dried and evaporated. The residue was recrystallized from EtOAc/hexane to give the title compound as a solid (280 mg, 0.56 mmol). Mp: 186–187° C.; NMR: 0.95 (d, 3H), 1.25 (d, 3H), 1.75 (s, 3H), 3.25 (dd, 1H), 3.35 (d, 1H), 3.5 (dd, 1H), 4.2 (m, 3H), 4.75 (s, 1H), 7.8 (d, 2H), 7.9 (d, 2H); m/z 418.

EXAMPLES 13–19

The procedure described in Example 12 was repeated using the appropriate acid chloride or sulphonyl chloride to replace the 4-cyanobenzene sulphonyl chloride to obtain the compounds described below.

| No | Example | m/z |
|---|---|---|
| 13 | (R)-[(2S,5R)-2-Methyl-5-methyl-4-(2-chloro-4-cyanophenylsulphonyl)-1-(3,3,3-trifluoro-2-hydroxy-2-methylpropionyl)piperazine] | 452 |
| 14 | (R)-[(2S,5R)-2-Methyl-5-methyl-4-(4-acetylphenylsulphonyl)-1-(3,3,3-trifluoro-2-hydroxy-2-methylpropionyl)piperazine] | 435 |
| 15 | (R)-[(2S,5R)-2-Methyl-5-methyl-4-(4-methoxyphenyl-sulphonyl)-1-(3,3,3-trifluoro-2-hydroxy-2-methylpropionyl)-piperazine] | 423 |
| 16 | (R)-[(2S,5R)-2-Methyl-5-methyl-4-(4-bromophenyl-sulphonyl)-1-(3,3,3-trifluoro-2-hydroxy-2-methylpropionyl)-piperazine] | 471 |
| 17 | (R)-[(2S,5R)-2-Methyl-5-methyl-4-(4-methoxybenzoyl)-1-(3,3,3-trifluoro-2-hydroxy-2-methylpropionyl)piperazine] | 387 |
| 18 | (R)-[(2S,5R)-2-Methyl-5-methyl-4-(4-dimethylaminobenzoyl)-1-(3,3,3-trifluoro-2-hydroxy-2-methylpropionyl)piperazine] | 330 |
| 19 | (R)-[(2S,5R)-2-Methyl-5-methyl-4-(4-bromobenzoyl)-1-(3,3,3-trifluoro-2-hydroxy-2-methylpropionyl)piperazine] | 435 |

EXAMPLE 20

(R)-[4-(4-Cyanobenzoylamino)-1-(3,3,3-trifluoro-2-hydroxy-2-methylpropionyl)piperidine]

To a solution of (R)-[4-amino-1-(3,3,3-trifluoro-2-hydroxy-2-methylpropionyl)piperidine] (Example 21, 170 mg, 0.71 mmol) and triethylamine (0.12 mg, 0.86 mmol) in EtOAc (15 ml) was added a solution of 4-cyanobenzoylchloride (130 mg, 0.78 mmol) in EtOAc (10 ml). The resultant mixture was stirred at ambient temperature for 4 hours, washed with 1 M hydrochloric acid, saturated sodium hydrogen carbonate solution and brine, dried and evaporated. The residue was chromatographed on silica with 50% EtOAc/DCM as eluent to give the title compound as a solid (97 mg, 0.26 mmol). NMR: 1.45 (m, 2H), 1.65 (s, 3H), 2.1 (m, 2H), 3.05 (m, 2H), 4.2 (m, 1H), 4.4–4.6 (m, 2H), 5.1 (s, 1H), 6.2 (d, 1H), 7.65 (d, 2H), 7.8 (d, 2H); m/z 368.

EXAMPLE 31

(R)-[4-Amino-1-(3,3,3-trifluoro-2-hydroxy-2-methylpropionyl)piperidine]

To a solution of 4-t-butyloxycarbonylaminopiperidine (Method C, 8.0 g, 40.0 mmol) and triethylamine (8.5 ml), 60 mmol) in DCM (200 ml) was added a solution of (S)-3,3,3-trifluoro-2-trimethylsilyloxy-2-methylpropanoyl chloride (*J. Med. Chem.*, 1999, 42, 2741–2746) (10.0 g, 41.3 mmol) in DCM (5 ml). The resultant mixture was stirred at ambient temperature overnight, the DCM evaporated, the residue taken up in EtOAc (150 ml), washed with saturated citric acid solution, saturated sodium hydrogen carbonate solution and brine, dried and evaporated. The residue was dissolved in methanol (25 ml), treated with saturated hydrogen chloride in methanol (100 ml), stirred at ambient temperature overnight and evaporated to dryness. The residue was recrystallized from methanol/EtOAc to give the title compound as the hydrochloride salt (7.5 g, 27.2 mmol). Mp: 245–246° C.; NMR: 1.45 (m, 2H), 1.5 (s, 3H), 1.95 (m, 2H), 3.25 (m, 1H), 4.4 (m, 2H), 4.65 (m, 2H), 7.15 (s, 1H), 8.2 (s, 3H); m/z (+ve ESP) 241 (M+H)$^+$.

EXAMPLE 22

(R)-[(2S)-2-Methyl-4-(4-cyanobenzoyl)-1-(3,3,3-trifluoro-2-hydroxy-2-metylpropionyl)piperazine]

4-Cyanobenzoyl chloride (0.30 g) was added to a stirred solution of the (R)-[2-(S)-methyl-1-(3,3,3-trifluoro-2-hydroxy-2-methylpropionyl)piperazine] (Example 27; 0.40 g) and triethylamine (0.30 ml) in DCM (10 ml). The reaction mixture was allowed to stir at room temperature for 17 hours (overnight), and then partitioned between DCM (20 ml) and 2 M HCl (20 ml). The organic phase was separated, dried and concentrated to give a gum. The residue was purified by chromatography on an 8 g silica Biotage cartridge eluting 1:1 EtOAc/isohexane to give the title compound (0.445 g) as a white solid. NMR (DMSO-d$_6$, 100° C.): 1.17 (d, 3H), 1.58 (s, 3H), 3.05–3.14 (m, 1H), 3.23–3.29 (m, 2H); 3.73 (brs, 1H), 3.88 (brs, 1H), 4.47 (d, 1H), 4.79 (brs, 1H), 6.79 (s, 1H), 7.58 (d, 2H), 7.88 (d, 2H); m/z 368.

EXAMPLES 23–25

The following compounds were prepared by the procedure of Example 22 using the appropriate benozyl or sulphonyl chloride.

| Ex | Compound | NMR(DMSO-d$_6$, 100° C.) | M/z |
|---|---|---|---|
| 23 | (R)-[(2S)-2-Methyl-4-(4-t-butylbenzoyl)-1-(3,3,3-trifluoro-2-hydroxy-2-methylpropionyl)piperazine] | 1.11(d, 3H), 1.32(s, 9H), 1.52(s, 3H), 3.03–3.10 (m, 1H), 3.20–3.26(m, 2H), 3.83(d, 1H), 3.94(d, 1H), 4.47(d, 1H), 4.76 (brs, 1H), 6.73(s, 1H), 7.32(d, 2H), 7.47(d, 2H) | 401 (M + H)$^+$ |
| 24 | (R)-[(2S)-2-Methyl-4-(4-bromophenylsulphonyl)-1-(3,3,3-trifluoro-2-hydroxy-2-methyl-propionyl)piperazine] | 1.23(d, 3H), 1.50(s, 3H), 2.40–2.47(m, 1H), 2.56 (d, 1H), 3.14–3.20(m, 1H), 3.45(d, 1H), 3.61(d, 1H), 4.58(d, 1H), 4.85(brs, 1H), 6.73(s, 1H), 7.67(d, 2H), 7.85(d, 2H) | 459 |
| 25 | (R)-[(2S)-2-Methyl-4-(4-isopropylphenyl-sulphonyl)-1-(3,3,3-trifluoro-2-hydroxy-2-methylpropionyl) piperazine] | 1.26(d, 3H), 1.29(d, 6H), 1.52(s, 3H), 2.35–2.41 (m, 1H), 2.51(d, 1H), 2.97–2.05(m, 1H), 3.14–3.20(m, 1H), 3.45 (d, 1H), 3.62(d, 1H), 4.55 (d, 1H), 4.85(brs, 1H), 6.76(s, 1H), 7.50(d, 2H), 7.70(d, 2H) | 421 |

EXAMPLE 26

(R)-[(2S)-2-Methyl-4-(2-nitrobenzenesulphonyl)-1-(3,3,3-trifluoro-2-hydroxy-2-methylpropionyl)piperazine]

To a stirred solution of (2S)-2-methyl-4-(2-nitrobenzenesulphonyl)piperazine (Method E; 14.1 g) in DCM (250 ml) at 0° C. was added triethylamine (20 ml) followed by a dropwise addition of the a solution of (S)-3,3,3-trifluoro-2-(trimethylsilyloxy)-2-methylpropanoyl chloride (prepared from (R)-3,3,3-trifluoro-2-hydroxy-2-methylpropionic acid (Method A) as described in *J. Med. Chem.*, 1999, 42, 2741–2746) (12.5 g) in DCM (50 ml). The reaction mixture was allowed to stir at ambient temperature overnight and was washed with HCl (2 M, 200 ml). The organic phase was separated, dried and volatile material was removed by evaporation to leave a pale yellow oil (25.97 g). This was re-dissolved in MeOH (250 ml) and HCl (2 M, 30 ml) was added and the reaction mixture was allowed to stir at ambient temperature overnight. Volatile material was removed by evaporation and the residue was partitioned between EtOAc (250 ml) and brine (200 ml). The organic phase was separated, dried and concentrated to leave a pale yellow glass (20.0 g). NMR: 1.32 (d, 3H), 1.68 (s, 3H), 2.77–2.88 (m, 1H), 2.98–3.03 (m, 1H), 3.46 (brs, 1H), 3.68 (d, 1H), 3.88 (d, 1H), 4.23 (brs, 1H), 4.89 (brs, 1H), 7.64–7.77 (m, 3H), 7.96 (d, 1H); m/z: 424.

EXAMPLE 27

(R)-[(2S)-2-Methyl-1-(3,3,3-trifluoro-2-hydroxy-2-methylpropionyl)piperazine]

To a stirred solution of (R)-[(2S)-2-methyl-4-(2-nitrobenzenesulphonyl)-1-(3,3,3-trifluoro-2-hydroxy-2-methylpropionyl)piperazine] (Example 26; 19.71 g) in anhydrous DMF (60 ml) was added thiophenol (5.5 ml) followed by anhydrous potassium carbonate (18.7 g). The reaction mixture was allowed to stir at ambient temperature under argon for 4 hours, filtered and washed with DCM (2×300 ml). The filtrate was acidified with HCl (2 M, 250 ml) and the organic phase was separated and discarded. The aqueous phase was adjusted to pH 8 with 2 M NaOH and extracted into EtOAc (5×300 ml). The organic layers were combined, dried and concentrated to give a pale yellow gum which slowly crystallized (4.88 g). NMR (DMSO-d$_6$, 100° C.): 1.21 (d, 3H), 1.54 (s, 3H), 2.49–2.55 (m, 1H), 2.65–2.75 (m, 3H), 2.82–2.91 (m, 2H), 2.97–3.01 (m, 1H), 4.31 (d, 1H), 4.60 (s, 1H); m/z (+ve ESP): 241 (M+H)$^+$.

PREPARATION OF STARTING MATERIALS

The starting materials for the Examples above are either commercially available or are readily prepared by standard methods from known materials. For example the following reactions are illustrations but not limitations of the preparation of some of the starting materials used in the above reactions.

Method A (R)-(+)-2-Hydroxy-2-methyl-3,3,3-trifluoropropanoic Acid (R/S)-2-Hydroxy-2-methyl-3,3,3-trifluoropropanoic acid was resolved according to the resolution method described in European Patent Application No. EP 524781 (described for the preparation of the (S)-(−)-acid) except that (1S,2R)-norephedrine was used in place of (1R,2S)-norephedrine or (S)-(−)-1-phenylethylamine to yield the title compound, $[\alpha]_D^{20}$ +18.1° C. (c, 8.8 in MeOH); NMR analysis of the acid in the presence of (R)-(+)-1-phenylethylaine gave an enantiomerical purity of >98%. NMR (CDCl$_3$): 1.27 (s, 3H) for the (R)-enantiomer, 1.21 (s, 3H) for the (S)-enantiomer.

Method B 5-(4-Methylsulphanylphenylsulphanyl)indoline

Tetrakis(triphenylphosphine)palladium(0) (0.99 g, 0.86 mmol) was added to a stirred solution of 5-bromoindoline (4.3 g, 21.7 mmol), 4-methylthiophenylthiol (3.4 g, 21.7 mmol) and sodium methoxide (2.4 g, 72.7 mmol) in anhydrous n-butanol (90 ml). The reaction mixture was heated under reflux with stirring for 6 hours then cooled and partitioned between EtOAc (200 ml) and brine (100 ml). The organic layer was separated, dried and volatile material was removed by evaporation. The residue was purified by flash column chromatography eluting with 0–30% EtOAc/isohexane to give the title compound (4.2 g, 15.3 mmol) as a solid. NMR: 2.43 (s, 3H), 3.03 (t, 2H), 3.6 (t, 2H), 6.58 (d, 1H), 7.05–7.27 (m, 6H); m/z (+ve ESP): 274 (M+H)$^+$.

Method C 4-t-Butyloxycarbonylaminopiperidine

1-Benzyl-4-t-butyloxycarbonylaminopiperidine (Method D, 5.4 g, 18.6 mmol) was dissolved in absolute ethanol (100 ml) and hydrogenated over 10% Pd/C for 24 hours at ambient temperature. The catalyst was removed by filtration and the filtrates evaporated to give the title compound (3.54 g, 17.7 mmol) which was used without further purification.

Method D

1-Benzyl-4-t-butyloxycarbonylaminopiperidine

To a stirred solution of 1-benzyl-4-aminopiperidine (3.8 g, 20 mmol) in water (20 ml) and t-butanol (20 ml) was added a solution of di-t-butyldicarbonate (5.24 g, 24 mmol) in t-butanol (20 ml). The mixture was heated at 50° C. for 2 hours, cooled to ambient temperature, the t-butanol evaporated, the aqueous residue extracted with EtOAc (2×50 ml), the combined EtOAc extracts washed with brine, dried and evaporated to give the title compound which was used without further purification.

Method E (2S)-2-Methyl-4-(2-nitrobenzenesulphonyl)piperazine

Sodium hydrogen carbonate (21.7 g) and acetone (50 ml) was added to a solution of (S)-(+)-2-methylpiperazine (6.0 g) in water (75 ml). The resulting suspension was cooled (0–5° C.) and a solution of 2-nitrobenzenesulphonyl chloride (15.9 g) in acetone (25 ml) was added, the reaction mixture was allowed to stir at ambient temperature overnight. Water (60 ml) was added and volatile material was removed by evaporation. The residue was acidified to pH 2 by the addition of HCl (2 M, 75 ml) and the mixture was extracted into DCM (2×100 ml). The aqueous phase was adjusted to pH 10–11 by the addition of NaOH (2 M, 50 ml) and extracted into EtOAc (2×150 ml). The organic washings were combined, dried and concentrated to leave the title compound (14.1 g) as a yellow oil. NMR: 1.06 (d, 3H), 2.35–2.43 (m,1H), 2.73–3.06 (m, 4H), 3.65–3.71 (m, 2H), 7.59–7.62 (m, 1H), 7.68–7.72 (m, 2H), 7.95–7.98 (m, 1H); m/z (+ve ESP): 286 (M+H)$^+$.

EXAMPLE 28

The following illustrate representative pharmaceutical dosage forms containing the compound of formula (I), or a pharmaceutically acceptable salt or in vivo hydrolysable ester thereof (hereafter compound X), for therapeutic or prophylactic use in humans:

| (a): Tablet I | mg/tablet |
|---|---|
| Compound X | 100 |
| Lactose Ph.Eur | 182.75 |
| Croscarmellose sodium | 12.0 |
| Maize starch paste(5% w/v paste) | 2.25 |
| Magnesium stearate | 3.0 |

| (b): Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone(5% w/v paste) | 2.25 |
| Magnesium stearate | 3.0 |

| (c): Tablet III | mg/tablet |
|---|---|
| Compound X | 1.0 |
| Lactose Ph.Eur | 93.25 |
| Croscarmellose sodium | 4.0 |
| Maize starch paste(5% w/v paste) | 0.75 |
| Magnesium stearate | 1.0 |

| (d): Capsule | mg/capsule |
|---|---|
| Compound X | 10 |
| Lactose Ph.Eur | 488.5 |
| Magnesium stearate | 1.5 |

| (e): Injection I | (50 mg/ml) |
|---|---|
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1 M Sodium hydroxide solution | 15.0% v/v |
| Water for injection | to 100% |

| (g): Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note
The above formulations may be obtained by conventional procedures well known in the pharmaceutical art. The tablets(a)–(c) may be enteric coated by conventional means, for example to provide a coating of cellulose acetate phthalate.

What is claimed is:

1. A compound of formula (I):

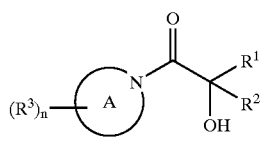

wherein:
Ring A is piperazinyl substituted on nitrogen by $R^4$—D—;

$R^1$ and $R^2$ are independently $C_k$alkyl optionally substituted by 1 to $2k+1$ atoms selected from fluoro and chloro wherein k is 1–3;

or $R^1$ and $R^2$ together with the carbon atom to which they are attached, form a $C_m$cycloalkyl ring optionally substituted by 1 to $2m-2$ fluorine atoms wherein m is 3–5;

$R^3$ is a substituent on carbon and is halo, hydroxy, cyano, formyl, amino, nitro, carboxy, carbamoyl, ureido, thiol, sulphamoyl or $R^5$—E—;

$R^4$ is $C_{1-6}$alkyl, phenyl or a heterocyclic group, wherein in $R^4$ any $C_{1-6}$alkyl, phenyl or heterocyclic group (on a ring carbon) may be optionally substituted by one or more $R^6$;

D is —N($R^9$)C(O)—, —S(O)$_2$— or —NS(O)$_2$—;

$R^5$ is $C_{1-6}$alkyl, wherein in $R^5$ any $C_{1-6}$alkyl may be optionally substituted by one or more $R^6$;

E is a direct bond;

$R^6$ is trifluoromethyl, $C_{1-6}$alkyl, halo, hydroxy, trifluoromethoxy, cyano, $C_{1-6}$alkoxy, formyl, $C_{1-6}$alkanoyl, $C_{1-6}$alkanoyloxy, amino, N-($C_{1-6}$alkyl)amino, N-($C_{1-6}$alkyl)$_2$amino, $C_{1-6}$alkanoylamino, $C_{1-6}$alkanoyl(N-$C_{1-6}$alkyl)amino, nitro, carboxy, carbamoyl, $C_{1-6}$alkoxycarbonyl, thiol, $C_{1-6}$alkylsulphanyl, $C_{1-6}$alkylsulphinyl, $C_{1-6}$alkylsulphonyl, $C_{1-6}$alkylsulphonylamino, sulphamoyl, N-($C_{1-6}$alkyl)aminosulphonyl, N-($C_{1-6}$alkyl)$_2$aminosulphonyl, N-($C_{1-6}$alkyl)carbamoyl, N-($C_{1-6}$alkyl)$_2$carbamoyl, ureido, N'-($C_{1-6}$alkyl)ureido or N'-($C_{1-6}$alkyl)$_2$ureido, $C_{2-6}$alkenyl, $C_{2-6}$alkynyl, $C_{3-6}$cycloalkyl, naphthyl or phenyl wherein in $R^6$ any $C_{1-6}$alkyl, $C_{2-6}$alkenyl, $C_{2-6}$alkynyl, $C_{3-6}$cycloalkyl, napthyl or phenyl may be optionally substituted by one or more $R^7$;

$R^7$ is trifluoromethyl, cyano, $C_{1-6}$alkyl, halo, hydroxy, trifluoromethoxy, $C_{1-6}$alkoxy, formyl, $C_{1-6}$alkanoyl, $C_{1-6}$alkanoyloxy, amino, N-($C_{1-6}$alkyl)amino, N-($C_{1-6}$alkyl)$_2$amino, $C_{1-6}$alkanoylamino, $C_{1-6}$alkanoyl(N-$C_{1-6}$alkyl)amino, nitro, carboxy, carbamoyl, $C_{1-6}$alkoxycarbonyl, thiol, $C_{1-6}$alkylsulphanyl, $C_{1-6}$alkylsulphinyl, $C_{1-6}$alkylsulphonyl, $C_{1-6}$alkylsulphonylamino, sulphamoyl, N-($C_{1-6}$alkyl)aminosulphonyl, N-($C_{1-6}$alkyl)$_2$aminosulphonyl, N-($C_{1-6}$alkyl)carbamoyl, N-($C_{1-6}$alkyl)$_2$carbamoyl, $C_{2-6}$alkenyl, $C_{2-6}$alkynyl or $C_{3-6}$cycloalkyl, and wherein in $R^7$ any $C_{1-6}$alkyl, $C_{2-6}$alkenyl, $C_{2-6}$alkynyl or $C_{3-6}$cycloalkyl groups may be optionally substituted by one or more groups selected from $R^{12}$;

wherein for $R^4$, a heterocyclic group is thienyl;

$R^9$ is hydrogen or $C_{1-6}$alkyl optionally substituted by one or more $R^{10}$ with the proviso that $R^{10}$ is not a substituent on the carbon attached to a nitrogen atom;

$R^{10}$ is halo, hydroxy, amino, cyano, nitro, trifluoromethyl, trifluoromethoxy, $C_{1-6}$alkyl, $C_{2-6}$alkenyl, $C_{2-6}$alkynyl, N-($C_{1-6}$alkyl)amino, N-($C_{1-6}$alkyl)$_2$amino, $C_{1-6}$alkanoylamino, $C_{1-6}$alkanoyl(N-$C_{1-6}$alkyl)amino, $C_{1-6}$alkylsulphonylamino, $C_{1-6}$alkylsulphonyl (N-$C_{1-6}$alkyl)amino, thiol, $C_{1-6}$alkylsulphanyl, $C_{1-6}$alkylsulphinyl, $C_{1-6}$alkylsulphonyl, sulphamoyl, N-($C_{1-6}$alkyl)aminosulphonyl, N-($C_{1-6}$alkyl)$_2$aminosulphonyl, carboxy, carbamoyl, N-($C_{1-6}$alkyl)carbamoyl, N-($C_{1-6}$alkyl)$_2$carbamoyl, $C_{1-6}$alkoxycarbonyl, $C_{1-6}$alkanoyl or formyl;

$R^{12}$ is halo, hydroxy, N-methylpiperazinyl, N-acetylpiperazinyl, morpholino, piperidino, cyano, amino, N,N-dimethylamino, acetamido, carbamoyl, carboxy, methanesulphonyl or sulphamoyl;

n is 0–5; wherein the values of $R^3$ may be the same or different;

or a pharmaceutically acceptable salt or an in vivo hydrolysable ester thereof.

2. A comopund of formula (I) according to claim 1 wherein one of $R^1$ and $R^2$ is methyl and the other is trifluoromethyl;

or a pharmaceutically acceptable salt or an in vivo hydrolysable ester thereof.

3. A compound of formula (I) according to claim 1 wherein $R^3$ is a substituent on carbon and is selected from amino and methyl;

or a pharmaceutically acceptable salt or an in vivo hydrolysable ester thereof.

4. A compound of formula (I) according to claim 1 wherein $R^4$ is $C_{1-4}$alkyl, phenyl {optionally substituted with one or more t-butyl, isopropyl, nitro, halo, N,N-dimethylcarbamoyl, N,N-dimethylamino, 2-hydroxyethylamino, cyano, acetyl, methoxy or carboxy} or thienyl;

or a pharmaceutically acceptable salt or an in vivo hydrolysable ester thereof.

5. A compound of formula (I) according to claim 1 wherein D is —SO$_2$—;

or a pharmaceutically acceptable salt or an in vivo hydrolysable ester thereof.

6. A compound of formula (I) according to claim 1 wherein n is 0–3;

or a pharmaceutically acceptable salt or an in vivo hydrolysable ester thereof.

7. A compound of formula (I) according to claim 1, selected from:

(R)-[(2S,5R)-2-methyl-5-methyl-4-(4-carboxyphenylsulphonyl)-1-(3,3,3-trifluoro-2-hydroxy-2-methylpropionyl)piperazine];

(R)-[(2S,5R)-2-methyl-5-methyl-4-(4-dimethylcarbamoylphenylsulphonyl)-1-(3,3,3-trifluoro-2-hydroxy-2-methylpropionyl)piperazine];

(R)-[(2S,5R)-2-methyl-5-methyl-4-(4-fluorophenylsulphonyl)-1-(3,3,3-trifluoro-2-hydroxy-2-methylpropionyl)piperazine];

(R)-{(2S,5R)-2-methyl-5-methyl-4-[4-(2-hydroxyethylamino)phenylsulphonyl]-1-(3,3,3-trifluoro-2-hydroxy-2-methylpropionyl)piperazine};

(R)-[(2S,5R)-2-methyl-5-methyl-4-(4-cyanophenylsulphonyl)-1-(3,3,3-trifluoro-2-hydroxy-2-methylpropionyl)piperazine]; and (R)-[(2S,5R)-2-methyl-5-methyl-4-(4-methoxyphenylsulphonyl)-1-(3,3,3-trifluoro-2-hydroxy-2-methylpropionyl)piperazine];

or a pharmaceutically acceptable salt or an in vivo hydrolysable ester thereof.

8. A process for preparing a compound of formula (I) as described in claim 1, or a pharmaceutically acceptable salt or an in vivo hydrolysable ester thereof, which process (in which variable groups are as defined in claim 1 for formula (I) unless otherwise state) comprises of:
(a) deprotecting a protected compound of formula (II):

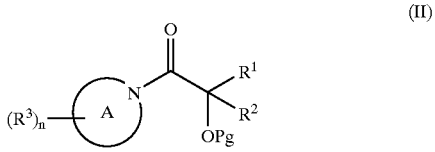

(II)

where Pg is an alcohol protecting group;
(b) coupling an amine of formula (III):

(III)

with an acid of formula (IV):

(IV)

wherein G is a hydroxyl group;
(c) coupling an amine of formula (III) with an activated acid derivative of formula (IV) wherein G is a hydroxyl group which may be protected as an ester or ether;
and thereafter if necessary:
  ii) removing any protecting groups; or
  iii) forming a pharmaceutically acceptable salt or in vivo hydrolysable ester.

9. A pharmaceutical composition which comprises a compound of formula (I) according to any one of claims 1–2 or 3–7, or a pharmaceutically acceptable salt or in vivo hydrolysable ester thereof in association with a pharmaceutically-acceptable diluent or carrier.

10. A method for the treatment of diabetes mellitus, said method comprising administering to a warm-blooded animal in need thereof a diabetes mellitus effective amount of a compound of the formula (I) or pharmaceutically acceptable salt or an in vivo hydrolysable ester thereof, as claimed in claims 1–2 or 3–7.

11. A method for the treatment of peripheral vascular disease, said method comprising administering to a warm-blooded animal in need thereof a peripheral vascular disease effective amount of a compound of the formula (I) or pharmaceutically acceptable salt or an in vivo hydrolysable ester thereof, as claimed in any one of claims 1–2 or 3–7.

12. A method for the treatment of myocardial or cerebral ischaemia, said method comprising administering to a warm-blooded animal in need thereof a myocardial or cerebral ischaemia effective amount of a compound of the formula (I) or pharmaceutically acceptable salt or an in vivo hydrolysable ester thereof, as claimed in any one of claims 1–2 or 3–7.

13. A method for the treatment of hyperlipidaemia, said method comprising administering to a warm-blooded animal in need thereof a hyperlipidaemia effective amount of a compound of the formula (I) or pharmaceutically acceptable salt or an in vivo hydrolysable ester thereof, as claimed in any one of claims 1–2 or 3–7.

* * * * *